US012778945B2

(12) United States Patent
Moraitis et al.

(10) Patent No.: US 12,778,945 B2
(45) Date of Patent: Nov. 3, 2026

(54) TREATMENTS FOR CUSHING'S SYNDROME THAT DO NOT SIGNIFICANTLY AFFECT CARDIAC RHYTHMS

(71) Applicant: Corcept Therapeutics Incorporated, Menlo Park, CA (US)

(72) Inventors: Andreas Moraitis, Sunny Isles Beach, FL (US); Joseph Custodio, Menlo Park, CA (US)

(73) Assignee: Corcept Therapeutics Incorporated, Redwood City, CA (US)

( * ) Notice: Subject to any disclaimer, the term of this patent is extended or adjusted under 35 U.S.C. 154(b) by 348 days.

(21) Appl. No.: 18/522,749

(22) Filed: Nov. 29, 2023

(65) Prior Publication Data

US 2024/0197716 A1 Jun. 20, 2024

Related U.S. Application Data

(60) Provisional application No. 63/526,274, filed on Jul. 12, 2023, provisional application No. 63/461,027, filed on Apr. 21, 2023, provisional application No. 63/429,003, filed on Nov. 30, 2022.

(51) Int. Cl.
*A61K 31/4745* (2006.01)
*A61P 5/46* (2006.01)

(52) U.S. Cl.
CPC ............ *A61K 31/4745* (2013.01); *A61P 5/46* (2018.01)

(58) Field of Classification Search
CPC .............................. A61K 31/4745; A61P 5/46
See application file for complete search history.

(56) References Cited

U.S. PATENT DOCUMENTS

2010/0179115 A1 7/2010 Belanoff
2012/0220565 A1 8/2012 Clark et al.
2021/0338643 A1* 11/2021 Moraitis .............. A61K 31/437

OTHER PUBLICATIONS

Alexandraki et al., "Specific Electrocardiogramasociated with Cushing's Disease", Clinical Endocrinology, vol. 74, May 2011, pp. 558-564.
O'neal et al., "The Association of the QT Interval with Atrial Fibrillation and Stroke: The Multi-Ethnic Study of Atherosclerosis", Clinical Research in Cardiology, vol. 104, Mar. 10, 2015, pp. 743-750.
International Patent Application No. PCT/US2023/081545 , "International Search Report and Written Opinion", Apr. 16, 2024, 12 pages.
International Patent Application No. PCT/US2023/081545, "International Preliminary Report on Patentability", Jun. 12, 2025, 8 pages.
EP Patent Application 23898778.8, Extended EP Search Report, mailed on Jun. 29, 2026, 14 pages.
Hunt, H., et al., "Assessment of Safety Tolerability, Pharmacokinetics, and Pharmacological Effect of Orally Administered CORT125134: An Adaptive, Double-Blind, Randomized, Placebo-Controlled Phase 1 Clinical Study", Clinical Pharmacology in Drug Development, vol. 7, No. 4, Oct. 2, 2017, pp. 408-421.
Hunt, H., et al., "1H-Pyrazolo [3,4-g]hexahydro-isoquinolines as Potent GR Antagonists with Reduced hERG Inhibition and an Improved Pharmacokinetic Profile", Bioorganic & Medicinal Chemistry Letters, vol. 25, No. 24, Dec. 1, 2015, pp. 5720-5725.
Hunt, H., et al., "Identification of the Clinical Candidate ( R)-(1-(4-Fluorophenyl)-6-((1-methyl-1 H-pyrazol-4-yl) sulfonyl)-4,4a,5,6,7,8-hexahydro-1 H -pyrazolo[3,4-g]isoquinolin-4a-yl) (4-(trifluoromethyl) pyridine-2-yl) methanone (CORT125134): A Selective Glucocorticoid Receptor (GR) Antagonist", Journal of Medicinal Chemistry, vol. 60, No. 8, Apr. 17, 2017, pp. 3405-3421.
Pivonello, R., et al., "Relacorilant, a Selective Glucocorticoid Receptor Modulator, Induces Clinical Improvements in Patients with Cushing Syndrome: Results from a Prospective, Open-Label Phase 2 Study", Frontiers in Endocrinology, vol. 12, Jul. 14, 2021, 12 pages.

(Continued)

*Primary Examiner* — Erich A Leeser
(74) *Attorney, Agent, or Firm* — James Fox; Kilpatrick Townsend & Stockton LLP

(57) ABSTRACT

Applicant discloses methods, uses, and compositions of heteroaryl ketone fused azadecalin compounds for treating patients suffering from Cushing's syndrome or Cushing's Disease (collectively "CS") without causing significant QT interval prolongation (e.g., the QT interval following administration differs by no more than about 10 milliseconds from the baseline QT interval). Therapeutic amounts of the heteroaryl ketone fused azadecalin compounds may be between about 50 milligrams per day (mg/day) and up to about 500 mg/day, and in embodiments may be up to about 800 mg/day. The methods, uses, and compositions may reduce QT interval, and may be useful for treating QT prolongation in patients, including CS patients. The treatments may be oral treatments administered to a fasted patient, or to a fed patient. The heteroaryl ketone fused azadecalin compounds may be administered with a meal. The heteroaryl ketone fused azadecalin compound may be relacorilant, which is (R)-(1-(4-fluorophenyl)-6-((1-methyl-1H-pyrazol-4-yl) sulfonyl)-4,4a,5,6,7,8-hexahydro-1H-pyrazolo[3,4-g]isoquinolin-4a-yl)(4-(trifluoromethyl)pyridine-2-yl)methanone, which has the structure:

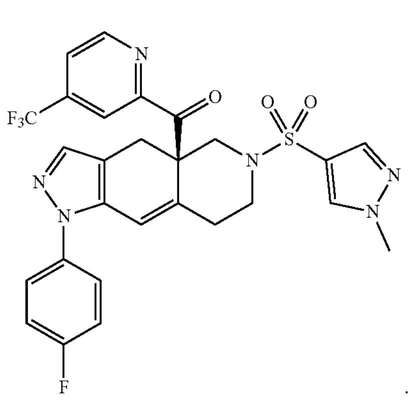

22 Claims, 11 Drawing Sheets

(56) References Cited

OTHER PUBLICATIONS

Donegan, D., et al., "Abstract #1403093: Absence of QT Prolongation Associated with Relacorilant, a Selective Glucocorticoid Receptor Modulator in Development for the Treatment of Cushing Syndrome—ScienceDirect", Endocrine Practice, vol. 29, No. 5, May.

Donegan, D., et al., "Relacorilant, a Selective Glucocorticoid Receptor Modulator in Development for the Treatment of Patients with Cushing Syndrome, Does Not Cause Prolongation of the Cardiac QT Interval", Endocrine Practice, vol. 30, No. 1, Jan. 1, 2024, pp. 11-18.

* cited by examiner

Schematic Diagram of Study Design

Model-Predicted placebo-corrected change from baseline QTcF (ΔΔQTcF)

Single Ascending Doses

Model-Predicted placebo-corrected change from baseline QTcF (ΔΔQTcF)

Multiple Ascending Doses

Placebo-Corrected Change from Baseline QTcF (ΔΔQTcF)

QTcF in Patients with CS (Low-dose group)

QTcF in Patients with CS (High-dose group)

TREATMENTS FOR CUSHING'S SYNDROME THAT DO NOT SIGNIFICANTLY AFFECT CARDIAC RHYTHMS

CROSS-REFERENCE TO RELATED APPLICATIONS

This application claims priority to U.S. Provisional Application Serial No. 63/429,003, filed Nov. 30, 2022; to U.S. Provisional Application Serial No. 63/461,027, filed Apr. 21, 2023; and to U.S. Provisional Application Serial No. 63/526,274, filed Jul. 12, 2023, all of which applications are hereby incorporated by reference herein in their entireties. This application claims priority to, and the benefit of, these parent applications.

BACKGROUND

A healthy heart with a healthy heart rhythm is important for a person's well-being. Electronic measurements of heart rhythms are termed electrocardiograms (ECGs). ECG measurements of cardiac activity include measured time intervals between salient ECG features detected by the ECG. The salient features of an ECG include the P wave, the QRS complex, and the T wave. The time interval between the beginning of the "QRS" complex and the end of the "T" wave is termed the "QT" interval. In healthy individuals, the "QT interval" is about 400 milliseconds (ms) (typically between about 350 ms and 450 ms). A QT interval greater than about 450 ms in men or greater than about 460 ms in women is considered a prolonged QT interval, and may indicate increased risk of cardiac arrhythmias, including the potentially fatal torsades de pointes.

Patients with prolonged QT interval may be at greater risk of fainting, seizures, atrial fibrillation, ventricular tachycardia, stroke, and even sudden death (Al-Khatib et al., JAMA 289(16):2120-2127 (2003); Soliman et al., Journal of the American College of Cardiology 59(16): 1460-1467 (2012)). Drug-induced prolongation of the QT interval is a risk factor for cardiovascular comorbidities including torsades de pointes, ventricular tachycardia, stroke, and sudden cardiac arrest (van Noord et al., *Br J Clin Pharmacol.* 2010; 70(1): 16-23; Roden D M. *N Engl J Med.* 2004; 350(10): 1013-1022; Raj et al., *Circulation.* 2009; 120(12):1123-1132.). Accordingly, regulatory authorities recommend thorough evaluation of QT interval prolongation and pro-arrhythmic potential of all new drug candidates.

Cortisol is a steroid hormone secreted by the adrenal glands due to the action of adrenocorticotropin hormone (ACTH). Cortisol action requires that cortisol bind to the glucocorticoid receptor (GR). Cushing's syndrome and Cushing's Disease (collectively "CS") are disorders of cortisol excess. Such cortisol excess may be due to any of several possible causes, including excess ACTH release from the pituitary gland, excess cortisol secretion from adrenal glands, or secretion of cortisol or ACTH from tumors. Long-term or excessive administration of glucocorticoids such as dexamethasone, prednisone, and others (which mimic cortisol action) can also cause CS.

A compound that modulates or affects cortisol binding to the GR is termed a GR modulator (GRM); a GRM that selectively modulates GR is termed a selective GRM (SGRM). Medical treatments for CS include GRMs and SGRMS (e.g., mifepristone); drugs that affect the production of cortisol (e.g., ketoconazole, levoketoconazole, and osilodrostat); and drugs that affect ACTH levels (e.g., pasireotide). However, to date, most of the drugs approved or widely used for treatment of CS are associated with QT interval prolongation, including pasoreotide (Colao et al., *N Engl J Med.* 2012; 366(10):914-924), osilodrostat (Fleseriu et al., *Pituitary.* 2016; 19(2):138-148), levoketoconazole (Fleseriu et al., *Lancet Diabetes Endocrinol.* 2019; 7(11): 855-865), and other drugs. Such QT interval prolongation may have very serious adverse effects on the patient.

The QT interval of male CS patients has been found to be greater than that of a matched control group of healthy male subjects (this difference was statistically significant; see Giraldi et al., Exp Clin Endocrinol Diabetes 2011, 119(4): 221-224). No difference was observed between female CS patients and a matched control group of healthy female subjects (Giraldi et al.). Thus, while both male and female CS patients treated by any of the CS drugs discussed above may be at risk of altered QT interval due to that drug treatment, male CS patients, already at risk of abnormal QT interval, may be at greater risk of abnormal heart rhythms than female CS patients treated with these drugs.

There is an unmet need for safe CS medications that do not adversely alter the heart rhythm, including medications that do not cause QT prolongation (which can cause possibly fatal arrhythmias). Accordingly, in order to reduce the risk of abnormal heart rhythms and associated adverse effects, improved methods and compositions for use in treating patients suffering from CS are needed that do not affect QT interval.

SUMMARY

Prolongation of QT interval is a serious side effect of prior CS drug treatments; QT prolongation increases the risk to the patient of serious heart arrhythmias that can lead to increased risk of heart attack, stroke, and sudden death, among multiple potential deleterious side effects of QT prolongation.

Disclosed herein are novel methods for treating Cushing's syndrome and Cushing's Disease (collectively "CS") without causing significant QT prolongation and without causing significant alteration of cardiac rhythms. The methods comprise administering to the subject an effective amount of a heteroaryl ketone fused azadecalin compound that modulates GRs. Heteroaryl ketone fused azadecalin compounds are disclosed in U.S. Pat. No. 8,859,774, the entire contents of which patent is hereby incorporated by reference in its entirety.

In embodiments, Applicants disclose methods of treating a patient suffering from CS without significantly prolonging the QT interval or the QTc interval, comprising:

Administering an effective amount of a heteroaryl ketone fused azadecalin compound, Wherein said treatment does not significantly prolong QT or QTc as measured by electrocardiogram (ECG), where QT is the duration of the time interval between the beginning of the QRS complex of the ECG and the end of the T wave of the ECG, and wherein QTc is the QT interval corrected for heart rate, Whereby the Cushing's syndrome or Cushing's Disease is treated without significantly prolonging the QT interval. In embodiments, the heteroaryl ketone fused azadecalin compound is a GRM, and in further embodiments, the heteroaryl ketone fused azadecalin compound is a SGRM, such as, e.g., relacorilant. Relacorilant is ((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl) pyridine-2-yl)methanone), which has the structure:

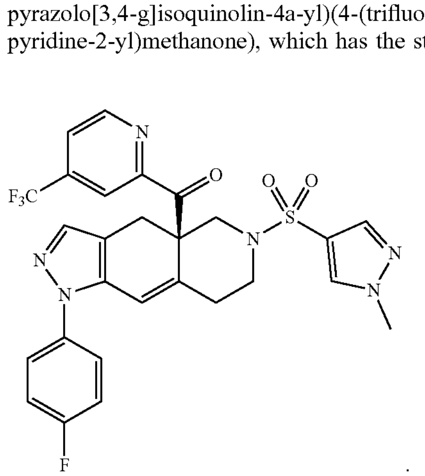

In embodiments, the GRM (e.g., a SGRM, such as relacorilant) is orally administered. In embodiments, the GRM or SGRM may be administered by injection, infusion, transdermal application, or by other means or routes of administration. In embodiments, the GRM or SGRM (e.g., relacorilant) may be administered with food, or with water, or with both food and water. In other embodiments, the GRM or SGRM (e.g., relacorilant) may be administered in the absence of food.

There is an unmet need for safe CS medications that do not cause QT prolongation and possibly fatal arrhythmias. Based on the present results from clinical studies in healthy volunteers and patients with CS, relacorilant is not associated with QT prolongation. Heteroaryl ketone fused azadecalin compounds such as relacorilant are believed to be able to fill this need. In addition to not causing QT prolongation, there is further an unmet need for safe CS medications that may reduce QT interval in patients in need thereof, including in CS patients with prolonged QT interval. Heteroaryl ketone fused azadecalin compounds such as relacorilant are believed to be able to fill this need as well.

Accordingly, the present methods provide improved methods of treating, and of reducing, prolonged QT interval in patients in need thereof. Thus, the present methods provide improved methods of treating CS patients which, unlike prior treatments, do not significantly prolong the cardiac QT interval, and do not significantly increase the risk to the CS patient of cardiac arrhythmias, torsades de pointes, sudden death, stroke, and other cardiac and cardiovascular disorders in CS patients.

BRIEF DESCRIPTION OF THE DRAWINGS

FIG. 3A shows changes in QTc over a period of 8 hours after single doses of 5 mg, 15 mg, or 50 mg relacorilant were administered. The doses were 5 mg (circles); 15 mg (squares); and 50 mg (triangles).

FIG. 3B shows changes in QTc over a period of 8 hours after single doses of 150 mg, 300 mg, or 500 mg relacorilant were administered. The doses were 150 mg (circles); 300 mg (squares); and 500 mg (triangles).

FIG. 3C shows changes in QTc over a period of 8 hours after the first of multiple daily doses of relacorilant were administered. The doses were 50 mg/day (circles); 150 mg/day (squares); 250 mg/day (upwardly pointing triangles); and 500 mg/day (downwardly pointing triangles).

FIG. 3D shows changes in QTc over a period of 8 hours after 7 days of multiple daily doses of relacorilant were administered. The doses were 50 mg/day (circles); 150 mg/day (squares); 250 mg/day (upwardly pointing triangles); and 500 mg/day (downwardly pointing triangles).

FIG. 3E shows changes in QTc over a period of 8 hours after 14 days of multiple daily doses of relacorilant were administered. The doses were 50 mg/day (circles); 150 mg/day (squares); 250 mg/day (upwardly pointing triangles); and 500 mg/day (downwardly pointing triangles).

DETAILED DESCRIPTION

Introduction

QT prolongation is a significant concern for patients with CS. About a quarter of men with present with QT prolongation (Giraldi et al. *Exp Clin EndocrinolDiabetes*2011; 119(4):221-224). Greater extent of QT prolongation correlates with greater risk of cardiac arrhythmic events, including the potentially fatal torsades de pointes. Cardiac arrhythmias are also related to increased risk of heart attack, stroke, and sudden death, among other serious, and potentially fatal, cardiac and cardiovascular disorders. Compounds used for prior CS treatments include levoketoconazole, ketoconazole, osilodrostat, pasireotide, mifepristone. All approved medical treatments for CS are associated with QT prolongation (see, e.g., levoketoconazole (RECORLEV®) and osilodrostat (ISTURISA®)).

Thus, there is an unmet need for safe CS medications that do not cause QT prolongation and do not cause possibly fatal arrhythmias or other serious cardiac and cardiovascular disorders. As disclosed herein, heteroaryl ketone fused azadecalin compounds, including the heteroaryl ketone fused azadecalin compound relacorilant, can meet such needs. Relacorilant administration does not cause QT prolongation.

There is a further unmet need for methods and treatments for reducing QT interval, and for treatments for QT prolongation in patients in need thereof. There is an unmet need for safe CS medications that may reduce QT interval in patients in need thereof, including in CS patients with prolonged QT interval. Heteroaryl ketone fused azadecalin compounds such as relacorilant may be used to provide improved methods of treating, and of reducing, prolonged QT interval in patients in need thereof, including CS patients. The methods, uses, and compositions disclosed herein may reduce QT interval, including for example, doses of about 400 mg/day, 500 mg/day, or up to 800 mg/day, and may be useful for treating QT prolongation in patients, including CS patients.

Figure 4A:
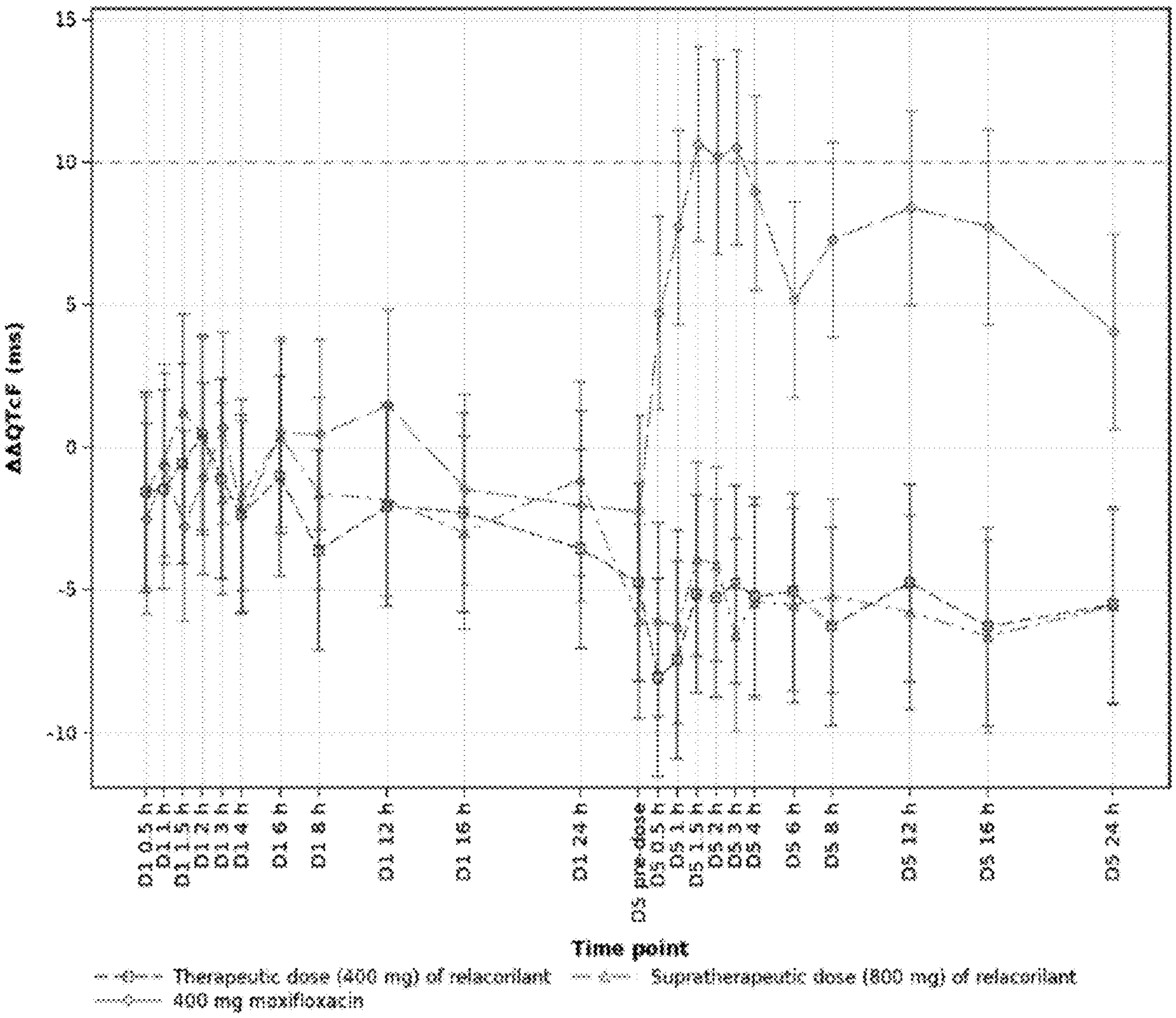
FIG. 4A shows the results of a TQT study on day 1 and day 5 of administration of relacorilant (400 mg (squares) or 800 mg (triangles) or of moxiflaxin (positive control; diamonds). Note that ΔΔQTcF appears to decline with time after relacorilant administration. These results exclude an adverse effect of relacorilant on ΔΔQTcF over 24 hours on day 1 or on day 5 of relacorilant administration. The dashed line shows the 10-msec ΔΔQTcF effect threshold.
Figure 4B:
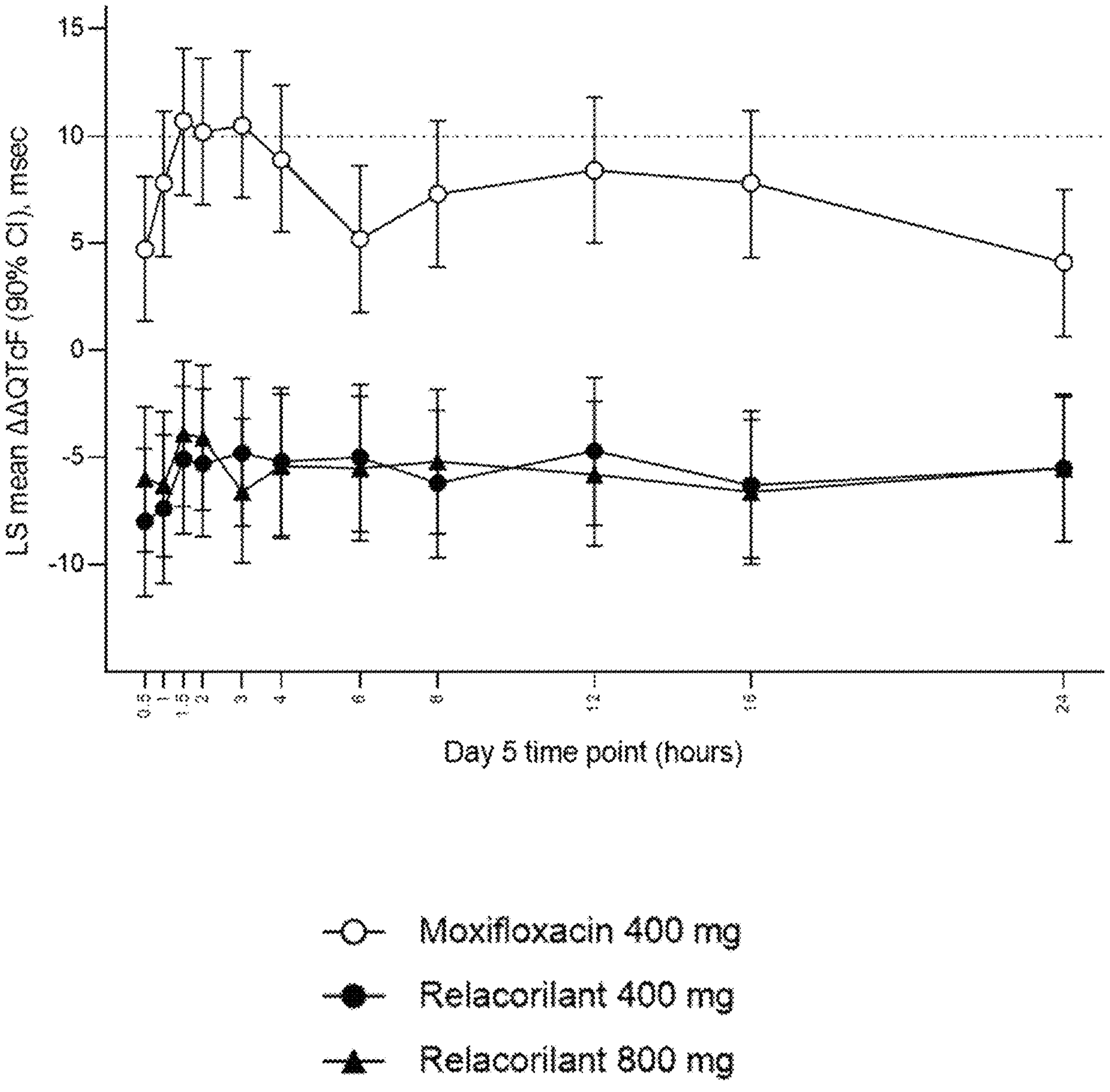
FIG. 4B shows the same results of a TQT study as shown in FIG. 4A, with FIG. 4B showing only day 5 of administration of relacorilant (400 mg (filled circles) or 800 mg (triangles) or of moxiflaxin (positive control; circles). These results exclude an adverse effect of relacorilant on ΔΔQTcF over 24 hours on day 5 of relacorilant administration. Baseline QTcF is the average of data extracted from ECG recordings taken at 45, 30, and 15 minutes pre-dose. In both FIGS. 4A and 4B, LS mean and 90% CI values were based on a linear mixed-effects model with ΔQTcF as the dependent variable and period, sequence, time, treatment, and time-by-treatment interaction as fixed effects, and with baseline QTcF as a covariate. The unstructured covariance matrix failed to converge, and an autoregressive structure was used to specify the repeated measures at post-dose time points for each participant during treatment. The dashed line shows the 10-msec ΔΔQTcF effect threshold.
Figure 5:
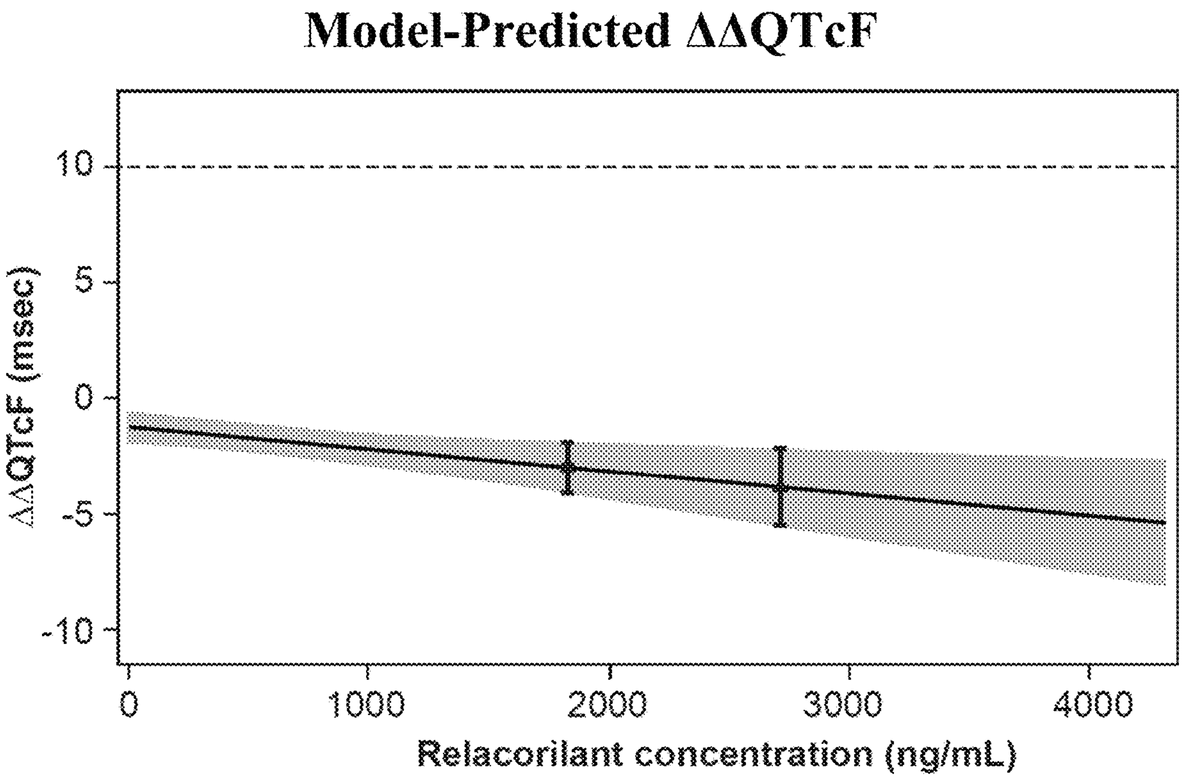
FIG. 5 shows the shows the results and theoretical modeling of the TQT study, the results of which exclude an adverse effect of relacorilant on ΔΔQTcF over the range of relacorilant concentrations up to about 4500 ng/ml. Markers and error bars: Estimated mean (90% CI) ΔΔQTcF at the observed geometric mean maximum relacorilant concentration with therapeutic (400 mg doses; square symbols) and supra-therapeutic (800 mg doses; triangular symbols) dosing. Dashed line: 10-ms ΔΔQTcF effect threshold. Solid line and shaded area: Predicted mean ΔΔQTcF with 90% CI, calculated from ΔΔQTcF=−1.2501 (msec)−0.97 (×10−3 msec/ng/mL)×relacorilant concentration (ng/mL). The solid black line and gray shaded area denote the model-predicted mean ΔΔQTcF and 90% CI, which was calculated from the equation ΔΔQTcF=−1.2501 (msec)−0.97 ($\times 10^{-3}$ msec/ng/mL)×relacorilant concentration (ng/ml). The square and triangular data points and error bars denote the estimated mean (90% CI) ΔΔQTcF at geometric mean relacorilant $C_{max}$ with therapeutic (400 mg) and supra-therapeutic (800 mg) dosing, respectively. The dashed line shows the 10-ms ΔΔQTcF effect threshold.
Figure 6A:
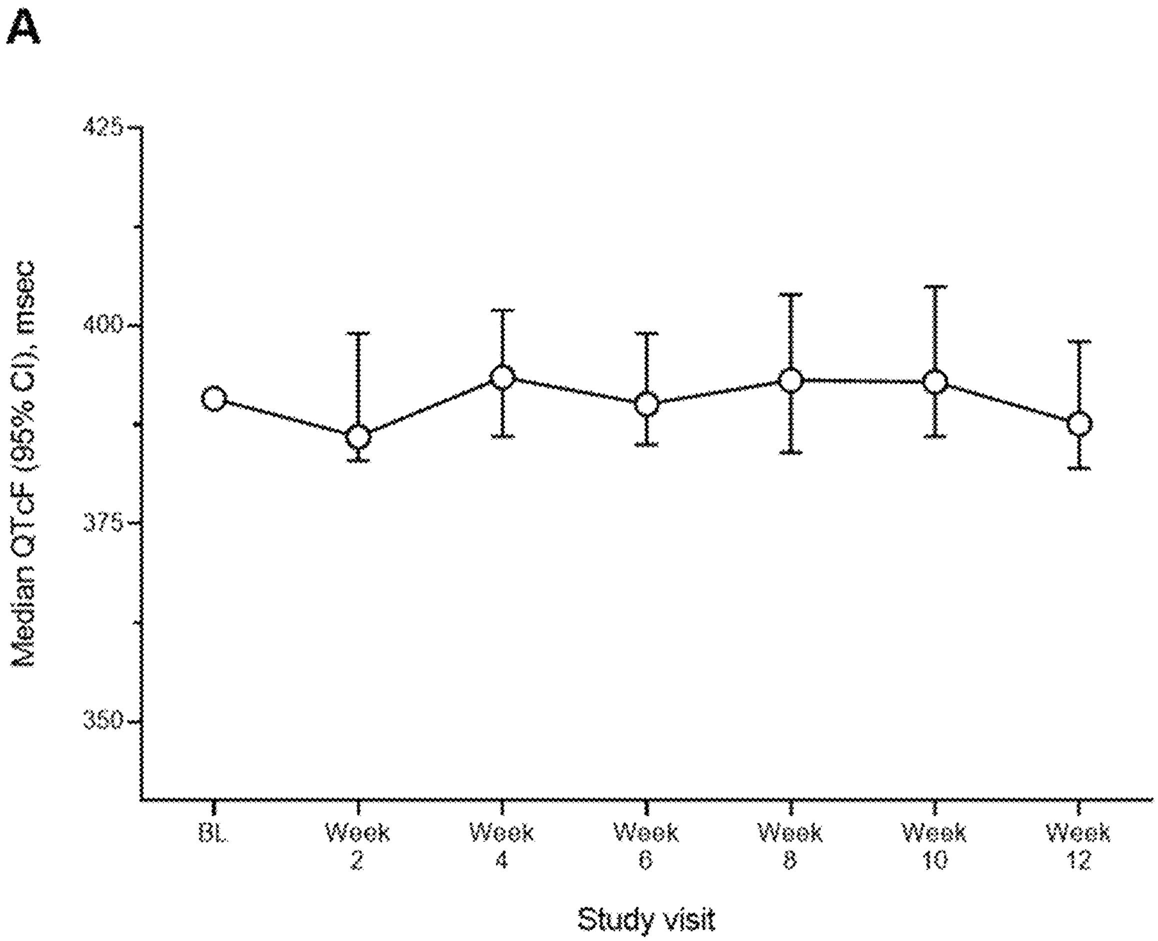
FIG. 6A shows the median QTcF values in CS patients receiving low doses of relacorilant (100 to 200 mg/day relacorilant). No significant changes in median QTcF were observed in the low-dose group. Data are median QTcF at baseline and median (95% CI) QTcF at weeks 2-16 and are based on 13-17 patients in the low-dose group. Baseline is defined as the average of the triplicate readings at the last visit prior to first dose of study drug. Low-dose relacorilant included 100 mg/day for 4 weeks, then 150 mg/day for 4 weeks, then 200 mg/day for 4 weeks. Abbreviations (throughout this application): BL=baseline; CS=Cushing syndrome.
Figure 6B:
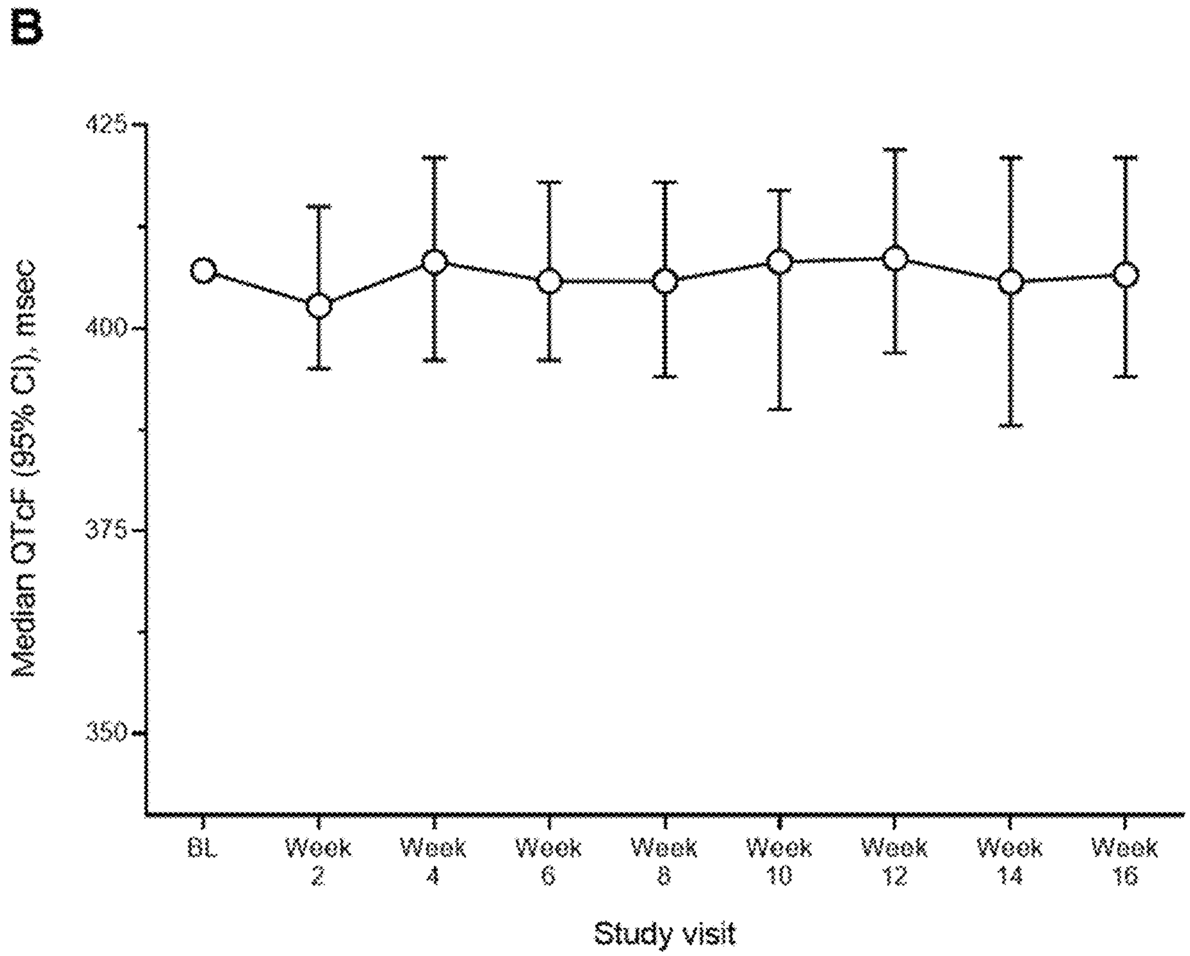
FIG. 6B shows the median QTcF values in CS patients receiving high doses of relacorilant (250 to 400 mg/day relacorilant). No significant changes in median QTcF were observed in the high-dose group. Data are median QTcF at baseline and median (95% CI) QTcF at weeks 2-16 and are based on 9-17 patients in the high-dose group. Baseline is defined as the average of the triplicate readings at the last visit prior to first dose of study drug. High-dose relacorilant included 250 mg/day for 4 weeks, then 300 mg/day for 4 weeks, then 350 mg/day for 4 weeks, then 400 mg/day for 4 weeks. Abbreviations (throughout this application): BL=baseline; CS=Cushing syndrome.

The present application demonstrates the absence of QT prolongation with relacorilant administration in healthy subjects (NCT03508635, the "phase 1 study"); in a Thorough QT study in healthy volunteers (NCT04795479, the "TQT study"); and in patients with CS (from a Phase 2 study in patients with CS, (NCT02804750, the "CS study"). Thus the heteroaryl ketone fused azadecalin compound relacorilant can be safely administered to patients at risk of suffering from QT prolongation, including CS patients, and can be safely administered to patients suffering from QT prolongation, including CS patients (e.g., male CS patients who suffer from QT prolongation). As discussed below, a trend toward reduced ΔΔQTcF was observed at higher relacorilant concentrations (FIGS. 2A and 2B) At the time of the highest concentration (2 h), a reduction in ΔΔQTcF was observed (FIGS. 3A-3E). FIGS. 4A and 4B shows that relacorilant (as doses of 400 mg and 800 mg) did not have an adverse effect on QT interval, while moxiflaxin did have such an adverse effect (as expected for that positive control compound). FIG. 5 shows the shows the clinical results, and related theoretical modeling, of QT in healthy volunteer subjects receiving relacorilant which exclude an adverse effect of relacorilant on ΔΔQTcF over the range of relacorilant concentrations up to about 4500 ng/ml. In FIGS. 6A and 6B, the results of studies in CS patients (receiving either low doses or high doses of relacorilant) show that there were no significant changes in median QTcF were observed in either dose group.

Thus, the present studies have shown that relacorilant maximum plasma concentrations ($C_{max}$) following administration of doses greater than 400 mg/day, e.g., doses of 800 mg/day, do not result in significant prolongation of the QT interval. (Prior studies of relacorilant used relacorilant doses of 500 mg/day or less.) Thus, heteroaryl ketone fused azadecalin compounds such as relacorilant may be administered to CS patients at doses greater than 400 mg/day without significantly increasing the risk of cardiac arrhythmias, and thus without significantly increasing the risk of heart attack, stroke, or sudden death, among multiple potential deleterious side effects of QT prolongation.

In embodiments, the present methods and uses may be applied to CS patients that are at high risk of QT prolongation, including CS patients with prolonged QT interval or prolonged QTc interval. Administering the heteroaryl ketone fused azadecalin compound relacorilant doesn't increase QT interval, and so its administration to CS patients with prolonged QT interval is not believed to increase the risk of arrhythmias and other cardiac and cardiovascular disorders in such CS patients. Since administering the heteroaryl ketone fused azadecalin compound relacorilant doesn't increase QT interval, its administration to CS patients with who are taking medications that prolong the QT interval is not believed to further increase the risk of arrythmias and other cardiac and cardiovascular disorders in such CS patients. Although administering relacorilant with food increases its bioavailability, and since administering the heteroaryl ketone fused azadecalin compound relacorilant doesn't increase QT interval, administering up to and greater than 400 mg relacorilant with food is not believed to increase the risk for arrythmias and other cardiac and cardiovascular disorders (as disclosed herein, amounts of 500 mg/day and 800 mg/day were safely administered to subjects).

In embodiments of the methods and uses disclosed herein, the QT interval of the patient measured after administration of said heteroaryl ketone fused azadecalin compound differs by no more than 10 milliseconds (ms or msec) from the patient's baseline QT interval measured prior to administration of the heteroaryl ketone fused azadecalin compound. In embodiments, the effective amount of the heteroaryl ketone fused azadecalin compound is between about 50 milligrams per day (mg/day) and about 400 mg/day, or about 500 mg/day. In further embodiments, the effective amount of the heteroaryl ketone fused azadecalin compound is between about 50 milligrams per day (mg/day) and about 800 mg/day. In embodiments, the heteroaryl ketone fused azadecalin compound is orally administered. In embodiments, the heteroaryl ketone fused azadecalin compound is administered to a fasted patient (i.e., a patient that has not eaten a meal for at least 4 hours prior to administration of the heteroaryl ketone fused azadecalin compound). In embodiments, the heteroaryl ketone fused azadecalin compound is administered to a fed patient (i.e., a patient that has eaten a meal less than one hour prior to administration of the heteroaryl ketone fused azadecalin compound). In embodiments, the heteroaryl ketone fused azadecalin compound is administered to the patient with a meal. In embodiments, the heteroaryl ketone fused azadecalin compound is relacorilant.

Relacorilant administration to healthy subjects led to a mild decrease in the QT interval (as measured by the heart-rate corrected QTc interval) compared to placebo in the study disclosed herein. For example, a trend toward reduced placebo-corrected change in QTc interval (ΔΔQTcF) was observed at higher relacorilant concentrations (a reduction in ΔΔQTcF was observed at 2 hours after relacorilant administration, which is the time of the maximum observed plasma concentration of relacorilant). Accordingly, it is believed that relacorilant may be useful for decreasing or normalizing the QTc interval in a patient with prolonged QTc interval.

Accordingly, Applicant discloses methods of treating a patient suffering from CS and suffering from prolonged QT interval, comprising: identifying the CS patient as suffering from prolonged QT interval, where the QT interval is the duration of the time interval between the beginning of the QRS complex of the ECG and the end of the T wave of the ECG, and administering an effective amount of a heteroaryl ketone fused azadecalin compound, such as relacorilant, said effective amount being between about 400 milligrams per day (mg/day) and about 800 mg/day of said heteroaryl ketone fused azadecalin compound, whereby the patient's CS and prolonged QT interval are treated. In embodiments, the effective amount of the heteroaryl ketone fused azadecalin compound is an amount between about 500 mg and about 800 mg. In embodiments, the patient is male.

Applicant discloses herein methods of decreasing the QT interval in a patient with a prolonged QT interval, where the QT interval is the duration of the time interval between the beginning of the QRS complex of the electrocardiogram (ECG) and the end of the T wave of the ECG, the method comprising administering an effective amount of a heteroaryl ketone fused azadecalin compound to said patient, such as an effective amount of relacorilant, whereby the patient's QT interval is decreased. In embodiments, the methods of decreasing the QT interval in a patient with a prolonged QT interval include a step of determining that the patient suffers from prolonged QT interval. In embodiments of the methods of decreasing the QT interval in a patient with a prolonged QT interval, the patient is male.

Applicant discloses herein the use of a heteroaryl ketone fused azadecalin compound, such as, e.g., relacorilant, for treating patients suffering from CS without significantly prolonging the QT interval of the patients. Applicant discloses herein the use of heteroaryl ketone fused azadecalin compounds, such as, e.g., relacorilant, in the manufacture of a medicament for treating patients suffering from CS without significantly prolonging the QT interval of the patients. Applicant discloses herein pharmaceutical compositions comprising a GRM heteroaryl ketone fused azadecalin compound, such as, e.g., the SGRM relacorilant, for treating patients suffering from CS without significantly prolonging the QT interval of the patients. Applicant discloses herein the use of a heteroaryl ketone fused azadecalin compound, such as, e.g., relacorilant, for reducing the QT interval in patients in need thereof, including in CS patients suffering from prolonged QT interval. Such uses include the use of heteroaryl ketone fused azadecalin compounds, such as, e.g., relacorilant, in the manufacture of a medicament for treating male patients.

Novel Methods and Uses of Heteroaryl Ketone Fused Azadecalins

Disclosed herein are novel methods, and uses of the disclosed compounds, for treating CS. The methods and uses provide treatment of patients suffering from CS without significantly affecting cardiac rhythms. For example, the methods and uses provide treatment of patients suffering from CS without significantly affecting the QT interval. The methods comprise administering to the subject an effective amount of a heteroaryl ketone fused azadecalin compound. Preferably, the heteroaryl ketone fused azadecalin compound is a GRM: compound that modulates GRs. In embodiments, the heteroaryl ketone fused azadecalin compound is a selective GRM (SGRM) compound which has little or no modulatory effect on other steroid hormone receptors (such as, e.g., a progesterone receptor, an aldosterone receptor, or an androgen receptor).

In embodiments of the methods and uses disclosed herein (including methods and uses for treating CS and methods and uses for reducing QT interval) comprise administering to the subject an effective amount of a heteroaryl ketone fused azadecalin compound, where a heteroaryl ketone compound is a compound described in U.S. Pat. No. 8,859,774 (which patent is hereby incorporated by reference in its entirety) having the following structure:

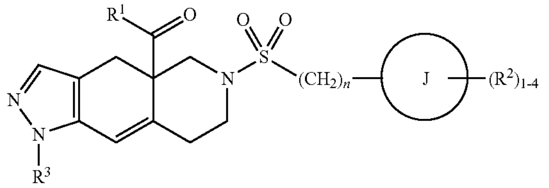

wherein $R^1$ is a heteroaryl ring having from 5 to 6 ring members and from 1 to 4 heteroatoms each independently selected from the group consisting of N, O and S, optionally substituted with 1-4 groups each independently selected from $R^{1a}$;

each $R^{1a}$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, —CN, N-oxide, $C_{3-8}$ cycloalkyl, and $C_{3-8}$ heterocycloalkyl;

ring J is selected from the group consisting of a cycloalkyl ring, a heterocycloalkyl ring, an aryl ring and a heteroaryl ring, wherein the heterocycloalkyl and heteroaryl rings have from κ to 6 ring members and from 1 to 4 heteroatoms each independently selected from the group consisting of N, O and S;

each $R^2$ is independently selected from the group consisting of hydrogen, $C_{1-6}$ alkyl, halogen, $C_{1-6}$ haloalkyl, $C_{1-6}$ alkoxy, $C_{1-6}$ haloalkoxy, $C_{1-6}$ alkyl-$C_{1-6}$ alkoxy, —CN, —OH, —$NR^{2a}R^{2b}$, —$C(O)R^{2a}$, —$C(O)OR^{2a}$, —$C(O)NR^{2a}R^{2b}$, —$SR^{2a}$, —$S(O)R^{2a}$, —$S(O)_2$ $R^{2a}$, $C_{3-8}$ cycloalkyl, and $C_{3-8}$ heterocycloalkyl, wherein the heterocycloalkyl groups are optionally substituted with 1-4 $R^{2c}$ groups;

alternatively, two $R^2$ groups linked to the same carbon are combined to form an oxo group (═O);

alternatively, two $R^2$ groups are combined to form a heterocycloalkyl ring having from 5 to 6 ring members and from 1 to 3 heteroatoms each independently selected from the group consisting of N, O and S, wherein the heterocycloalkyl ring is optionally substituted with from 1 to 3 $R^{2d}$ groups;

$R^{2a}$ and $R^{2b}$ are each independently selected from the group consisting of hydrogen and $C_{1-6}$ alkyl;

each $R^{2c}$ is independently selected from the group consisting of hydrogen, halogen, hydroxy, $C_{1-6}$ alkoxy, $C_{1-6}$ haloalkoxy, —CN, and —$NR^{2a}R^{2b}$;

each $R^{2d}$ is independently selected from the group consisting of hydrogen and $C_{1-6}$ alkyl, or two $R^{2d}$ groups attached to the same ring atom are combined to form (═O);

$R^3$ is selected from the group consisting of phenyl and pyridyl, each optionally substituted with 1-4 $R^{3a}$ groups;

each $R^{3a}$ is independently selected from the group consisting of hydrogen, halogen, and $C_{1-6}$ haloalkyl; and subscript n is an integer from 0 to 3;

or salts and isomers thereof.

In embodiments, methods for treating CS and methods for reducing QT interval disclosed herein comprise administering to the subject an effective amount of the SGRM heteroaryl ketone fused azadecalin compound relacorilant. Relacorilant (also referred to as "CORT125134") is ((R)-(1-(4-fluorophenyl)-6-((1-methyl-1H-pyrazol-4-yl)sulfonyl)-4,4a,5,6,7,8-hexahydro-1H-pyrazolo[3,4-g]isoquinolin-4a-yl)(4-(trifluoromethyl)pyridine-2-yl)methanone), which has the structure:

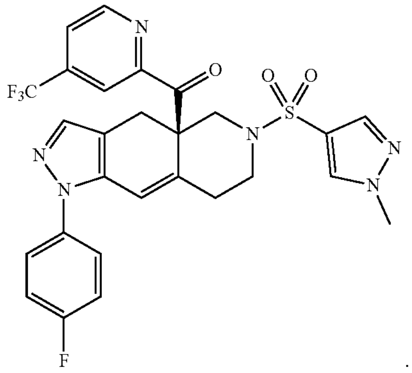 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

Relacorilant is disclosed in Example 18 of U.S. Pat. No. 8,859,774, which patent is hereby incorporated by reference in its entirety.

In embodiments, the methods disclosed herein can be used to treat a patient suffering from CS by administering an effective amount of a heteroaryl ketone fused azadecalin GRM or SGRM, along with another CS treatment, effective to treat CS without causing significant QT prolongation.

In embodiments of the methods disclosed herein, an effective amount of a heteroaryl ketone fused azadecalin GRM or SGRM (e.g., relacorilant) is administered to a patient suffering from CS effective to treat the patient. Such administration may be daily administration (e.g., once per day, or twice per day, or three times per day) or may be administration at other intervals (e.g., once every other day, or once every three days, or other interval). In embodiments, an effective amount for the treatment of CS by administration of a GRM or SGRM such as relacorilant may be, e.g., 50 milligrams (mg), or 75 mg, or 100 mg, or 150 mg, or 200 mg, or 225 mg, or 250 mg, or 300 mg, or 325 mg, or 350 mg, or 375 mg, or 400 mg, or 425 mg, or 450 mg, or 475 mg, or 500 mg, or 525 mg, or 550 mg, or 575 mg, or 600 mg, or 625 mg, or 650 mg, or 675 mg, or 700 mg, or 725 mg, or 750 mg, or 775 mg, or 800 mg, or other amount, effective to treat CS. In embodiments, the heteroaryl ketone fused azadecalin GRM or SGRM (e.g., relacorilant) may be administered orally, and may be administered along with food, or along with water, or along with both food and water. Typically, administration of the GRM (e.g., a SGRM, such as relacorilant) is once-daily administration; however, in embodiments, administration may be twice daily, or three times daily, or may be every other day, or every three days, or every four days, or at other intervals as necessary or convenient. Administration of the heteroaryl ketone fused azadecalin GRM or SGRM (e.g., relacorilant) may continue for weeks, months, or years as needed; e.g., relacorilant administration may continue for weeks, months, or years as needed.

An effective amount of relacorilant, or other GRM or SGRM, may be administered to the patient orally, e.g., by mouth, in a capsule, pill, tablet, fluid, emulsion, or other composition suitable for oral administration. Relacorilant may be administered along with food, or along with water, or along with both food and water. In other embodiments, the GRM (e.g., relacorilant) may be administered in the absence of food, and may be administered to a fasted subject or patient in the absence of food.

Definitions

As used herein, the term "AE(s)" is an acronym for Adverse Event(s).

As used herein, the term "AR" refers to the Accumulation Ratio (a ratio between the plasma exposures at steady state and the plasma exposures on the first day of dosing).

As used herein, the term "AUC" refers to the area under the plasma concentration-time curve calculated using the linear up/log down trapezoidal method.

As used herein, the term "$AUC_{0-24}$" refers to the AUC from time zero to hour 24 post dose.

As used herein, the term "$AUC_{0-tau}$" refers to the AUC from time zero to the end of the dosing interval.

As used herein, the term "$AUC_{inf}$" refers to the AUC from time 0 extrapolated to infinity.

As used herein, the term "$AUC_{last}$" refers to the AUC from time 0 to time of the last measurable concentration (Clast).

As used herein, the terms "beat" and "heartbeat" refer to a single heartbeat, including the T wave, QRS complex, and P wave. The T wave, QRS complex, PR interval, QT interval, P wave, and other features of the ECG are defined as accepted in the art (see, e.g., FIGS. 2-25 and text on pages 40-41 of *Cardiovascular Physiology*, by Berne and Levy, 3rd Edition, 1977).

As used herein, the term "$C_{avg}$" refers to the Average concentration over a dosing interval.

As used herein, the term "$C_{max}$" refers to the Maximum observed plasma concentration.

As used herein, the term "$C_{min}$" refers to the Minimum observed plasma concentration over a dosing interval.

As used herein, the term "Δ" refers to the Change-from-baseline.

As used herein, the term "ΔΔ" refers to the Placebo-corrected change-from-baseline.

As used herein, the term "ECG" an acronym for the Electrocardiogram.

As used herein, "Fridericia's Formula" is $QTcF=(QT)/(RR^{1/3})$.

As used herein, the term "FI" refers to the Fluctuation Index (an assessment of the variation observed in the peak plasma concentrations to the trough plasma-concentrations during the dosing interval).

As used herein, the term "HR" refers to the heart rate.

As used herein, the term "ΔHR" refers to the change in the heart rate from baseline.

As used herein, the term "ΔΔHR" refers to the placebo-corrected change-from-baseline of the heart rate.

As used herein, the term "mean (SD)" refers to the mean of a set of data points±the standard deviation of that set of data points.

Moxifloxacin is a fluoroquinolone compound, sold as Avelox® as the monohydrochloride salt of 1-cyclopropyl-7-[(S,S)-2,8-diazabicyclo[4.3.0]non-8-yl]-6-fluoro-8-methoxy-1,4-dihydro-4-oxo-3 quinoline carboxylic acid for clinical use as an antibiotic. Moxifloxacin has been shown to prolong the QT interval of the electrocardiogram in some patients. Its chemical structure is

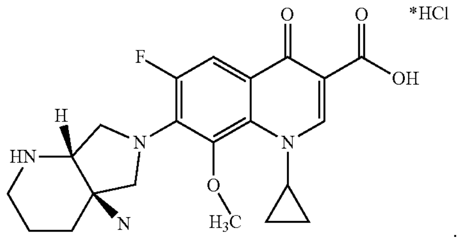 [SMILES: COc1c(N2C[C@H]3NCCC[C@@]3(N)C2)c(F)cc2c(=O)c(C(=O)O)cn(C3CC3)c12]

As used herein, the phrase "multiple ascending dose" and its acronym "MAD" refer to the administration of more than one dose of a test drug (e.g., relacorilant) to each of a group of subjects and the results obtained from those subjects following such administration. Each subject receives an initial low dose, and subsequent increased doses of the test drug.

As used herein, the term "PR" refers to the PR interval of the ECG.

As used herein, the term "ΔPR" refers to the change in the PR interval from baseline.

As used herein, the term "ΔΔPR" refers to the placebo-corrected change-from-baseline of the PR interval.

As used herein, the term "QD" refers to once-daily drug administration.

As used herein, the term "QRS" refers to the QRS interval of the ECG.

As used herein, the term "ΔQRS" refers to the change in the QRS interval from baseline.

As used herein, the term "ΔΔQRS" refers to the placebo-corrected change-from-baseline of the QRS interval.

As used herein, the term "QT interval" refers to the QT interval of the ECG, which is the interval from the onset of ventricular depolarization to the end of ventricular repolarization (the time interval between the beginning of the "QRS" complex and the end of the "T" wave of the ECG). In healthy individuals, the "QT interval" is about 400 milliseconds (ms) (typically between about 350 ms and 450 ms). As used herein, the term "QT interval" refers both to the interval between the beginning of the QRS complex and the end of the T wave; as such, the term QT interval includes the uncorrected interval and also the heart-rate corrected QT interval "QTc" however calculated, including QTcF, the QTc calculated according to Fredericia's Formula.

As used herein, the term "QTc" refers to the Corrected QT interval of the ECG corrected for heart rate. One method for calculating QTc is to divide the measured QT interval by the square root of the RR interval (the interval between successive R peaks of successive QRS complexes) (other methods divide by the third root of the RR interval, or use linear regression methods; see, e.g., Al-Khatib et al., JAMA 289 (16):2120-2127 (2003)).

As used herein, the term "QTcF" refers to the QT interval of the ECG corrected for heart rate using Fridericia's Formula. QTcF is calculated using Fridericia's Formula by dividing the measured QT interval by the third-root of the RR interval: $QTcF=(QT)/(RR^{1/3})$.

As used herein, the term "ΔΔQTcF" refers to the placebo-corrected change-from-baseline QTcF.

As used herein, the term "an adverse effect" as applied to the placebo-corrected ΔQTcF (ΔΔQTcF) indicates an increase in ΔΔQTcF (indicating a prolonged QT interval). A numerical value is typically applied regarding "an adverse effect", e.g., "an adverse effect>10 msec" means that any increase in ΔΔQTcF was less than 10 msec.

As used herein, the terms "prolonged QT interval", "significant QT prolongation", and the like refer to an increase in QT interval or QTc interval, as compared to the patient's baseline QT interval or baseline QTc interval, of greater than 10 msec. Where the patient's baseline QT interval is not known, a QT interval greater than about 450 ms in men or greater than about 470 ms in women is considered to be a prolonged QT interval. A QTcF interval is considered to be a high QTcF interval if it is greater than about 500 ms in patients with a wide QRS interval (a QRS interval is a wide QRS interval if it is greater than about 120 ms).

As used herein, the term "RR" refers to the RR interval of the ECG.

As used herein, the phrase "single ascending dose" and its acronym "SAD" refer to the administration of a single dose of a test drug (e.g., relacorilant) to a group of subjects (typically healthy volunteer subjects) and the results obtained from those subjects following such administration. Typically, a low dose is administered to a first group of subjects; and a larger dose is next administered to a different group of subjects; further larger doses may be given to yet further different groups of subjects to provide data regarding a range of doses of the test drug.

As used herein, the term "SAE(s)" is an acronym for Serious Adverse Event(s).

As used herein, the term "$t_{1/2}$" refers to the apparent terminal elimination half-life.

As used herein, the term "$T_{max}$" refers to the time after dosing to reach maximum plasma concentration ($C_{max}$).

As used herein, the term "TEAE(s)" is an acronym for Treatment Emergent Adverse Event(s).

As used herein, the term "TQT" is an acronym for Thorough QT/QTc, i.e., a study directed to assessing the effect of a drug, such as moxifloxacin or relacorilant, on cardiac repolarization. As used herein, the effect on cardiac repolarization was assessed by the drug effects (or lack thereof) on the corrected QT (QTc) interval.

As used herein, the term "patient" refers to a human that is or will be receiving, or has received, medical care for a disease or condition, such as, e.g., CS.

As used herein, the term "effective amount" or "therapeutic amount" refers to an amount of a pharmacological agent effective to treat, eliminate, or mitigate at least one symptom of the disease being treated. In some cases, "therapeutically effective amount" or "effective amount" can refer to an amount of a functional agent or of a pharmaceutical composition useful for exhibiting a detectable therapeutic or inhibitory effect. The effect can be detected by any assay method known in the art.

As used herein, the terms "significant" and "significantly", as used to characterize a change in a value or an effect, indicate a change in a value or a change in an effect that would be expected to have a clinical effect. For example, a significant change in QT interval or QTc interval is a change that is greater than 10 milliseconds (ms) as compared to a baseline QT interval or QTc interval.

As used herein, the terms "substantial" and "substantially", as used to characterize a change in a value or an effect, indicate a change in a value or a change in an effect that would be expected to have a clinical effect. For example, a substantial change in QT interval or QTc interval is a change that is greater than 10 milliseconds (ms) as compared to a baseline QT interval or QTc interval.

As used herein, the terms "administer," "administering," "administered" or "administration" refer to providing a compound or a composition (e.g., one described herein), to a subject or patient. For example, a compound or composition may be administered orally to a patient (i.e., the subject receives the compound or composition via the mouth, as a pill, capsule, liquid, or in other form suitable for administration via the mouth. Oral administration may be buccal (where the compound or composition is held in the mouth, e.g., under the tongue, and absorbed there). Administration may be by injection, i.e., delivery of the compound or composition via a needle, microneedle, pressure injector, or other means of puncturing the skin or forcefully passing the compound or composition through the skin of the subject. Injection may be intravenous (i.e., into a vein); intraarterial (i.e., into an artery); intraperitoneal (i.e., into the peritoneum); intramusucular (i.e., into a muscle); or by other route of injection. Routes of administration may also include rectal, vaginal, transdermal, via the lungs (e.g., by inhalation), subcutaneous (e.g., by absorption into the skin from an implant containing the compound or composition), or by other route.

As used herein, the term "combination therapy" refers to the administration of at least two pharmaceutical agents to a subject to treat a disease. The two agents may be administered simultaneously, or sequentially in any order during the entire or portions of the treatment period. The at least two agents may be administered following the same or different dosing regimens.

As used herein, the term "glucocorticoid receptor" ("GR") refers to the type II GR, a family of intracellular receptors which specifically bind to glucocorticoids such as cortisol and/or cortisol analogs such as dexamethasone (See, e.g., Turner & Muller, J. Mol. Endocrinol. Oct. 1, 2005 35 283-292). (The term "glucocorticoid" may be abbreviated as "GC".) The type II glucocorticoid receptor is also referred to as the cortisol receptor. The term includes isoforms of GR, recombinant GR and mutated GR.

The term "glucocorticoid receptor modulator" (GRM) refers to any compound which modulates glucocorticoid binding to GR, or which modulates any biological response associated with the binding of GR to an agonist. For example, a GRM that acts as an agonist, such as dexamethasone, increases the activity of tyrosine aminotransferase (TAT) in HepG2 cells (a human liver hepatocellular carcinoma cell line; ECACC, UK). A GRM that acts as an antagonist, such as mifepristone, decreases the activity of tyrosine aminotransferase (TAT) in HepG2 cells. TAT activity can be measured as outlined in the literature by A. Ali et al., J. Med. Chem., 2004, 47, 2441-2452.

As used herein, the term "selective glucocorticoid receptor modulator" (SGRM) refers to a selective GRM, that is, a composition or compound which selectively modulates glucocorticoid binding to GR, or selectively modulates any biological response associated with the binding of a GR to an agonist. By "selective," the drug preferentially binds to the GR rather than other nuclear receptors, such as the progesterone receptor (PR), the mineralocorticoid receptor (MR) or the androgen receptor (AR). It is preferred that the selective glucocorticoid receptor modulator bind GR with an affinity that is 10× greater ($1/10^{th}$ the $K_d$ value) than its affinity to the MR, AR, or PR, both the MR and PR, both the MR and AR, both the AR and PR, or to the MR, AR, and PR. Relacorilant is a SGRM.

As used herein, the term "compound" is used to denote a molecular moiety of unique, identifiable chemical structure. A molecular moiety ("compound") may exist in a free species form, in which it is not associated with other molecules. A compound may also exist as part of a larger aggregate, in which it is associated with other molecule(s), but nevertheless retains its chemical identity. A solvate, in which the molecular moiety of defined chemical structure ("compound") is associated with a molecule(s) of a solvent, is an example of such an associated form. A hydrate is a solvate in which the associated solvent is water. The recitation of a "compound" refers to the molecular moiety itself (of the recited structure), regardless of whether it exists in a free form or an associated form.

As used herein, the term "composition" is intended to encompass a product comprising the specified ingredients such as the said compounds, their tautomeric forms, their derivatives, their analogues, their stereoisomers, their polymorphs, their deuterated species, their pharmaceutically acceptable salts, esters, ethers, metabolites, mixtures of isomers, their pharmaceutically acceptable solvates and pharmaceutically acceptable compositions in specified amounts, as well as any product which results, directly or indirectly, from combination of the specified ingredients in the specified amounts. Such term in relation to a pharmaceutical composition is intended to encompass a product comprising the active ingredient(s), and the inert ingredient(s) that make up the carrier, as well as any product which results, directly or indirectly, in combination, complexation or aggregation of any two or more of the ingredients, or from dissociation of one or more of the ingredients, or from other types of reactions or interactions of one or more of the ingredients. Accordingly, the pharmaceutical compositions of the present invention are meant to encompass any composition made by admixing compounds of the present invention with pharmaceutically acceptable carriers.

As used herein, the terms "pharmaceutically acceptable excipient" and "pharmaceutically acceptable carrier" refer to a substance that aids the administration of an active agent to—and absorption by—a subject and can be included in the compositions of the present invention without causing a significant adverse toxicological effect on the patient. These terms are intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. One of ordinary skill in the art will recognize that other pharmaceutical excipients are useful in the present invention.

"Salt" refers to acid or base salts of the compounds used in the methods disclosed herein. Illustrative examples of pharmaceutically acceptable salts are mineral acid (hydrochloric acid, hydrobromic acid, phosphoric acid, and the like) salts, organic acid (acetic acid, propionic acid, glutamic acid, citric acid, and the like) salts, and quaternary ammonium (methyl iodide, ethyl iodide, and the like) salts. It is understood that the pharmaceutically acceptable salts are non-toxic. Additional information on suitable pharmaceutically acceptable salts can be found in Remington's Pharmaceutical Sciences, 17th ed., Mack Publishing Company, Easton, Pa., 1985, which is incorporated herein by reference.

Pharmaceutical Compositions and Administration

In embodiments, the present invention provides a pharmaceutical composition for treating CS, the pharmaceutical composition including a pharmaceutically acceptable excipient and a GRM such as, e.g., relacorilant. In some embodiments, the pharmaceutical composition includes a pharmaceutically acceptable excipient and a SGRM. In preferred embodiments, the pharmaceutical composition includes relacorilant and a pharmaceutically acceptable excipient or excipients.

Suitable formulations can be prepared and administered in a wide variety of oral, parenteral and topical dosage forms. GRMs and SGRMs can be administered orally. For example, the GRM can be administered as a pill, a capsule, or liquid formulation as described herein. Oral preparations include tablets, pills, powder, dragees, capsules, liquids, lozenges, gels, syrups, slurries, suspensions, etc., suitable for ingestion by the patient. Alternatively, GRMs and SGRMs can also be administered by injection, that is, intravenously, intramuscularly, intracutaneously, subcutaneously, intraduodenally, or intraperitoneally.

For preparing pharmaceutical compositions from GRMs and SGRMs, pharmaceutically acceptable carriers can be either solid or liquid. Solid form preparations include powders, tablets, pills, capsules, cachets, suppositories, and dispersible granules. A solid carrier can be one or more substances, which may also act as diluents, flavoring agents, binders, preservatives, tablet disintegrating agents, or an encapsulating material. Details on techniques for formulation and administration are well described in the scientific and patent literature, see, e.g., the latest edition of Remington's Pharmaceutical Sciences, Mack Publishing Co, Easton PA ("Remington's").

In powders, the carrier is a finely divided solid, which is in a mixture with the finely divided active component, a heteroaryl ketone fused azadecalin GRM or SGRM, e.g., relacorilant. In tablets, the active component is mixed with the carrier having the necessary binding properties in suitable proportions and compacted in the shape and size desired.

The powders and tablets preferably contain from 5% or 10% to 70% of the active compound (e.g., relacorilant). Suitable carriers are magnesium carbonate, magnesium stearate, talc, sugar, lactose, pectin, dextrin, starch, gelatin, tragacanth, methylcellulose, sodium carboxymethylcellulose, a low melting wax, cocoa butter, and the like. The term "preparation" is intended to include the formulation of the active compound with encapsulating material as a carrier providing a capsule in which the active component with or without other carriers, is surrounded by a carrier, which is thus in association with it. Similarly, cachets and lozenges are included. Tablets, powders, capsules, pills, cachets, and lozenges can be used as solid dosage forms suitable for oral administration.

Suitable solid excipients are carbohydrate or protein fillers which may include, but are not limited to, sugars including lactose, sucrose, mannitol, or sorbitol; starch from corn, wheat, rice, potato, or other plants; cellulose such as methyl cellulose, hydroxypropylmethyl-cellulose, or sodium carboxymethylcellulose; and gums including arabic and tragacanth; as well as proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound (i.e., dosage). Pharmaceutical preparations of the invention can also be used orally using, for example, push-fit capsules made of gelatin, as well as soft, sealed capsules made of gelatin and a coating such as glycerol or sorbitol. Push-fit capsules can contain GR modulator mixed with a filler or binders such as lactose or starches, lubricants such as talc or magnesium stearate, and, optionally, stabilizers. In soft capsules, the GR modulator compounds may be dissolved or suspended in suitable liquids, such as fatty oils, liquid paraffin, or liquid polyethylene glycol with or without stabilizers.

Liquid form preparations include solutions, suspensions, and emulsions, for example, water or water/propylene glycol solutions. Liquid formulations may include a salt, such as, e.g., sodium chloride, or a sugar, such as, e.g., sucrose. For parenteral injection, liquid preparations can be formulated in solution in aqueous polyethylene glycol solution.

The pharmaceutical compositions disclosed herein can be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preparation may be a lyophilized powder in 1 mM-50 mM histidine, 0.1%-2% sucrose, 2%-7% mannitol at a pH range of 4.5 to 5.5, that is combined with buffer prior to use.

Also included are solid form preparations, which are intended to be converted, shortly before use, to liquid form preparations for oral administration. Such liquid forms include solutions, suspensions, and emulsions. These preparations may contain, in addition to the active component, colorants, flavors, stabilizers, buffers, artificial and natural sweeteners, dispersants, thickeners, solubilizing agents, and the like.

Oil suspensions can be formulated by suspending a SGRM in a vegetable oil, such as arachis oil, olive oil, sesame oil or coconut oil, or in a mineral oil such as liquid paraffin; or a mixture of these. The oil suspensions can contain a thickening agent, such as beeswax, hard paraffin or cetyl alcohol. Sweetening agents can be added to provide a palatable oral preparation, such as glycerol, sorbitol or sucrose. These formulations can be preserved by the addition of an antioxidant such as ascorbic acid. As an example of an injectable oil vehicle, see Minto, *J. Pharmacol. Exp. Ther.* 281:93-102, 1997. The pharmaceutical formulations of the invention can also be in the form of oil-in-water emulsions. The oily phase can be a vegetable oil or a mineral oil, described above, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan mono-oleate, and condensation products of these partial esters with ethylene oxide, such as polyoxyethylene sorbitan mono-oleate. The emulsion can also contain sweetening agents and flavoring agents, as in the formulation of syrups and elixirs. Such formulations can also contain a demulcent, a preservative, or a coloring agent.

The pharmaceutical preparation is preferably in unit dosage form. In such form the preparation is subdivided into unit doses containing appropriate quantities of the active component, a GRM or SGRM such as, e.g., relacorilant. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

The quantity of active component in a unit dose preparation may be varied or adjusted from 1 mg to 1000 mg, or 10 mg to 800 mg, or, e.g., 50 mg to 500 mg. Suitable dosages also include about 10 mg, 20, 30, 40, 50, 60, 70, 75, 80, 90, 100, 150, 200, 250, 300, 400, 500, 600 mg, 700 mg, or 800 mg, according to the particular application and the potency of the active component. The composition can, if desired, also contain other compatible therapeutic agents.

The formulations should provide a sufficient quantity of active agent to effectively treat CS. Thus, in one embodiment, the pharmaceutical formulation for oral administration of a GRM such as relacorilant is in a daily amount of between about 1 to about 20 mg per kilogram of body weight per day (mg/kg/day), or in a daily amount from about 1.5 to 15 mg/kg/day, or from about 2 to 10 mg/kg/day.

In some embodiments, the GRM is administered in one dose. For example, a GRM may be administered in a single dose given once per day. In other embodiments, the GRM is administered in more than one dose, e.g., 2 doses, 3 doses, 4 doses, 5 doses, 6 doses, 7 doses, or more. In some cases, the doses are of an equivalent amount. In other cases, the doses are of different amounts. The doses can increase or taper over the duration of administration. The amount may vary according to, for example, patient characteristics.

Any suitable GRM dose may be used in the methods disclosed herein. A suitable GRM dose may be a daily dose, or may be a dose that is administered with other timing (e.g., twice per day, or once every other day, or once every three days, or at other intervals). The dose of GRM, e.g., relacorilant, that is administered can be at least about 50 milligrams (mg), or about 75 mg, e.g., about 100 mg, about 150 mg, about 200 mg, about 225 mg, about 250 mg, about 300 mg, about 350 mg, about 375 mg, about 400 mg, about 450 mg, about 500 mg, about 525 mg, about 600 mg, about 650 mg, about 700 mg, about 750 mg, about 800 mg, or more. In embodiments, the GRM is administered orally. In some embodiments, the GRM is administered in at least one dose. In other words, the GRM can be administered in 1, 2, 3, 4, 5, 6, 7, 8, 9, 10 or more doses. In embodiments, the GRM is administered orally in 1, 2, 3, 4, 5, 6, 7, 8, 9, 10 or more doses.

The duration of treatment with a GRM or SGRM to treat CS can vary according to the severity of the condition in a subject and the subject's response to GRMs or SGRMs. In embodiments, the treatment may continue as long as needed. In embodiments, the treatment may continue as long as the patient is capable of receiving oral medication. In some embodiments, relacorilant may be administered for a period of up to about 2 years or more. In embodiments, administration of a heteroaryl ketone fused azadecalin GRM or SGRM, such as relacorilant, may continue for 1, 2, 3, 4, 5, 10, 15, 20, 24, 30, 36, 48, 50, 52, 100, 104, 156, or 208 weeks, or longer, as needed to treat the patient. In embodiments, administration of a GRM such as relacorilant may continue for as long as the patient needs such administration, or for as long as the patient remains capable of receiving such GRM administration.

In some embodiments, administration of a GRM or SGRM is not continuous and can be stopped for one or more periods of time, followed by one or more periods of time where administration resumes. Suitable periods where administration stops include 1 to 10 weeks, 2 to 8 weeks, 3 to 6 weeks, and 4 to 5 weeks.

GRMs and SGRMs can be used in combination with other active agents known to be useful in modulating a glucocorticoid receptor, or with adjunctive agents that may not be effective alone, but may contribute to the efficacy of the active agent.

After a pharmaceutical composition including a GR modulator of the invention has been formulated in an acceptable carrier, it can be placed in an appropriate container and labeled for treatment of an indicated condition. For administration of a GRM or SGRM, such labeling would include, e.g., instructions concerning the amount, frequency and method of administration.

EXAMPLE

The following example is provided by way of illustration only and not by way of limitation. Those of skill in the art will readily recognize a variety of noncritical parameters which could be changed or modified to yield essentially similar results.

Example. Evaluation of Relacorilant Effects on Cardiac Rhythms

The studies disclosed herein evaluated the cardiac effects of the heteroaryl ketone fused azadecalin compound relacorilant by determining the effects of therapeutic and supra-therapeutic plasma concentrations of relacorilant on the heart rate-corrected QT interval (QTc) in healthy subjects and in Cushing's syndrome (CS) patients. These studies showed that relacorilant did not increase QT interval, and that there was a trend towards lower QT interval with the higher doses of relacorilant. Other observations and results included evaluations of the effect of relacorilant on other electrocardiogram (ECG) parameters, including heart rate (HR), PR and QRS intervals, and T-wave morphology; and evaluating the safety and tolerability of therapeutic and supra-therapeutic oral doses of relacorilant in healthy subjects.

The results of three studies of relacorilant are included in the present application: a phase 1, placebo-controlled single- and multiple-ascending dose (SAD/MAD) study (up to 500 mg relacorilant over up to 14 days) in healthy volunteers (NCT03508635); a phase 1 placebo- and positive-controlled thorough QTc study of therapeutic (400 mg) and supra-therapeutic (800 mg) doses of relacorilant in healthy volunteers performed in accordance with International Council of Harmonisation (ICH) regulatory guidelines (NCT04795479); and a phase 2, open-label study of low-dose (200 mg) and high-dose (400 mg) relacorilant administered daily for up to 16 weeks in patients with endogenous CS (NCT02804750). All study participants had normal QTc at the start of the respective studies. Continuous ECG recordings were taken at baseline/pre-dose, and changes in QTc from baseline at multiple post-dose timepoints were calculated. Association of plasma relacorilant concentrations with effect on QTc interval was assessed using a linear mixed-effects modeling approach.

In an aspect, these studies evaluated the safety and tolerability of therapeutic and supra-therapeutic oral doses of relacorilant in healthy subjects. The therapeutic dose of relacorilant was set as 400 mg/day, in accordance with the relacorilant daily therapeutic dose range of between 100 mg to 400 mg in studies regarding the treatment of CS and oncologic indications. Data for the effect of food on relacorilant demonstrated that maximum plasma concentrations ($C_{max}$) of relacorilant were only increased approximately 34% and 41% upon administration with a high-fat or moderate-fat breakfast, respectively, relative to fasting conditions. In addition, clinical data for relacorilant indicated that drug-drug interactions and food effects would only result in small, transient increases in relacorilant plasma concentrations in patients receiving the highest clinical dose of 400 mg/day. Additionally, the FDA has set a relacorilant exposure limit of 40,000 ng*h/mL and has advised that it is unnecessary to achieve multiples of the highest exposure scenario in the presence of a separate positive control. Therefore, these studies included moxifloxacin 400 mg as a positive control and the supratherapeutic dose of relacorilant was set conservatively as 800 mg/day (twice the therapeutic dose of relacorilant). At the supratherapeutic dose of 800 mg once daily for 5 days, the plasma concentrations of relacorilant and its metabolites were expected to exceed those achieved in patients at the highest therapeutic dose of 400 mg/day.

These studies included a randomized, partial double-blind, placebo- and positive-controlled, multiple-dose, 4-way crossover, thorough QT/QTc (TQT) study to investigate the effect of relacorilant on cardiac repolarization. These studies measured placebo-corrected change-from-baseline QTcF (ΔΔQTcF); change-from-baseline of QTcF, HR, and PR and QRS intervals (ΔQTcF, ΔHR, ΔPR, and ΔQRS); placebo-corrected change-from-baseline of HR, and PR and QRS intervals (ΔΔHR, ΔΔPR, and ΔΔQRS); categorical outliers for QTcF, HR, and PR and QRS intervals; the frequency of treatment-emergent changes of T-wave morphology and presence of U-waves; PK parameters of relacorilant and its metabolites (CORT125337, CORT125336, and CORT125295) and moxifloxacin; safety profiles, including AEs/SAEs, physical examination, clinical chemistry, hematology, urinalysis, ECG, and vital signs.

These studies included a "First-in-Human" study in healthy volunteers; a "Thorough QT" (TQT) study in healthy volunteers, and a study in patients suffering from Cushing's syndrome (CS study). These studies are briefly summarized as follows:

First-In-Human Study

A phase 1, 3-part, single-center, First-in-Human study (NCT03508635) included 103 healthy volunteers who received single or multiple ascending doses (SAD/MAD) of relacorilant (up to 500 mg QD) for up to 14 days; 24 received placebo.

TQT Study

A phase 1, randomized, partial double-blind, crossover thorough QT study (NCT04795479) to assess the effect of multiple doses of relacorilant on cardiac repolarization in healthy volunteers. Participants were randomized to dosing sequences to receive relacorilant at therapeutic (400 mg QD, n=25) or supra-therapeutic (800 mg QD, n=28) doses, or placebo (n=29) for 5 days. Moxifloxacin (400 mg single dose, n=28) was used as a positive control.

CS Study

A single-arm, open-label phase 2 study (NCT02804750) in patients with CS. 17 patients received low-dose relacorilant (100-200 mg QD) for 12 weeks; 18 patients received high-dose relacorilant (250-400 mg QD) for 16 weeks.

In all studies, ECG data were collected and the heart rate-corrected QT interval using Fridericia's formula (QTcF) was calculated. Participants with a family history of or risk factors for torsades de pointes or with a prolonged QT interval at screening were not eligible to participate. Exposure-response analysis of the effect of relacorilant on the heart-rate corrected QT interval (QTc) was conducted using a linear model with an intercept.

Relacorilant was administered orally to the subjects via 100 mg, softgel capsules. The study included administration of relacorilant to 103 healthy volunteers (receiving single or ascending doses of up to 500 mg once per day (mg QD) of relacorilant). The study also included administration of multiple doses of relacorilant of 400 mg QD (n=25, "therapeutic dose") and 800 mg QD (n=28, "supratherapeutic dose") to healthy volunteers. The study further included administration of relacorilant (100-200 mg QD (n=17, low dose) or 250-400 mg QD (n=18, high dose)) to CS patients. No significant QT prolongation associated with relacorilant administration was observed in the study.

Figure 1:
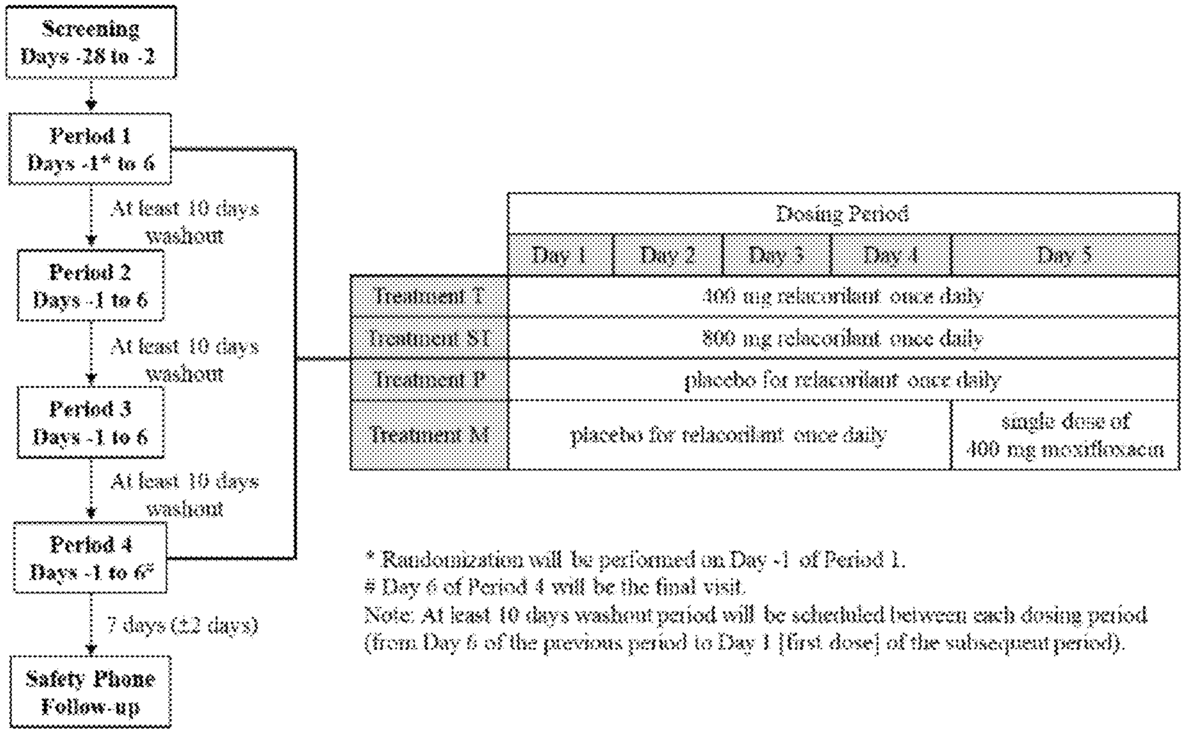
FIG. 1 shows a schematic diagram of the study protocol.

A schematic diagram of the study protocol is presented in FIG. 1.

Main Inclusion Criteria

Healthy male and female subjects aged 18-55 years old with a body mass index (BMI) ≥18.0 kg/m2 and ≤30.0 kg/m2 and adequate cardiac conduction by electrocardiogram (ECG) without any clinical significant abnormality. Subjects with a marked baseline prolongation of ECG intervals, including QTcF>450 milliseconds (msec), PR>200 msec, or QRS>120 msec, or with resting heart rate<45 bpm or >100 bpm were not enrolled in this study. The incidence of AEs/SAEs and the results of physical examination, clinical serum chemistry, hematology, urinalysis, ECG, and vital signs were analyzed in enrolled subjects as part of the study.

Safety assessments included adverse event (AE) or serious adverse event (SAE) monitoring during the entire study period and physical examination, clinical chemistry, hematology, urinalysis, safety ECG assessment, and vital signs performed during each dosing period. When ECG extractions coincided with safety ECGs, vital signs assessment and blood draws, procedures were carried out in said order. The total amount of blood collected from each subject was approximately 470 mL during the entire study period, including screening procedures and 4 dosing periods.

Measurements

ECG measurements: During each dosing period, cardiodynamic replicate ECGs were collected and extracted from a continuous (Holter) recording at 3 time points prior to dosing on Day 1 (−45, −30, and −15 minutes before dosing) and once prior to dosing on Day 5 at approximately the same time as the collection of blood samples from the subjects and at 0.5, 1, 1.5, 2, 3, 4, 6, 8, 12, 16, and 24 hours post-dose on Day 1 and Day 5.

Pharmacokinetic (PK) Parameters

PK analyses were performed using non-compartmental methods to obtain estimates of the following parameters, where possible:

For relacorilant and its metabolites (CORT125337, CORT125336, and CORT125295):

Day 1: $C_{max}$, $T_{max}$, $AUC_{last}$, and $AUC_{0-24}$;

Day 5: $C_{max}$, $T_{max}$, $C_{min}$, $AUC_{last}$, $AUC_{0-tau}$, $C_{avg}$, FI, and AR.

For moxifloxacin: $C_{max}$, $T_{max}$, $AUC_{last}$, and $AUC_{0-24}$.

During each period, blood samples were collected at pre-dose and 0.5, 1, 1.5, 2, 3, 4, 6, 8, 12, 16, and 24 hours post-dose on Day 1 and Day 5 during each dosing period. PK blood sampling for Day 1 was completed prior to dosing on Day 2. The plasma concentration data for relacorilant and its metabolites (CORT125337, CORT125336, and CORT125295) or moxifloxacin were determined using a validated liquid chromatography with tandem mass spectrometry (LC-MS/MS).

Criteria for Evaluation

ECG parameters: The primary endpoint was the placebo-corrected change-from-baseline QTcF (ΔΔQTcF). The secondary endpoints included:

- Change-from-baseline of QTcF, HR, PR, QRS intervals (ΔQTcF, ΔHR, ΔPR, and ΔQRS);
- Placebo-corrected change-from-baseline HR, PR, and QRS (ΔΔHR, ΔΔPR, and ΔΔQRS);
- Categorical outliers for QTcF, HR, PR, and QRS;
- Frequency of treatment-emergent changes of T-wave morphology and U-waves presence.

Study Treatment

Each subject received 4 treatments in a randomized sequence during the study period. Each dosing consisted of 8 capsules (except for moxifloxacin on Day 5), including:

- Treatment T: Multiple oral doses of 400 mg relacorilant (4 capsules)+placebo for relacorilant (4 capsules) once daily for 5 days;
- Treatment ST: Multiple oral doses of 800 mg relacorilant (8 capsules) once daily for 5 days;
- Treatment P: Multiple oral doses of placebo for relacorilant (8 capsules) once daily for 5 days;
- Treatment M: Multiple oral doses of placebo for relacorilant (8 capsules) once daily for 4 days and a final single oral dose of 400 mg moxifloxacin (one tablet) on Day 5.

Subjects were randomized to one of 12 dosing sequences on Day-1 of Period 1 after the confirmation of subjects' eligibility. Randomization was performed by the contracted contract research organization (CRO) compliant with relevant SOPs. The randomization scheme and code were generated using SAS® software.

Fasting/Meals During Confinement

Subjects were admitted to the clinical site in the morning on Day-1 (one day prior to dosing, check-in day) of each dosing period. After check-in, subjects stayed at the clinical site until the morning of Day 6 during each dosing period. Meals were served on Day-1 in each period before fasting overnight for at least 10 hours prior to dosing in the next morning (Day 1) of each dosing period. Water was allowed ad lib during the study confinement period, except for 1 hour before and after dosing. During this confinement period, standardized meals and beverages were served. A standardized meal is defined as low-fat meals in which ≤20% of caloric intake comes from fat.

In a portion of present study conducted in healthy subjects, a single dose of moxifloxacin (400 mg; Treatment M) on the last day of its respective treatment period was included as a positive control to determine the sensitivity of the study to detect small QTc changes. Relacorilant doses included both a therapeutic dose level (400 mg; Treatment T) and a supra-therapeutic dose level (800 mg; Treatment ST). The study was blinded to subjects, investigator, study staff, and sponsor with respect to relacorilant (Treatments T and ST) and placebo for relacorilant (Treatment P); it was open-labeled for moxifloxacin (Treatment M). Enrolled subjects were randomized to one of twelve (12) dosing sequences to receive 4 different treatments according to the assigned dosing sequence as shown below:

Dosing Sequences

| Sequence | 1 | 2 | 3 | 4 | 5 | 6 | 7 | 8 | 9 | 10 | 11 | 12 |
|---|---|---|---|---|---|---|---|---|---|---|---|---|
| Period 1 Treatment | T | ST | P | M | ST | P | T | M | P | T | ST | M |
| Period 2 Treatment | ST | M | T | P | P | M | ST | T | T | M | P | ST |
| Period 3 Treatment | P | T | M | ST | T | ST | M | P | ST | P | M | T |
| Period 4 Treatment | M | P | ST | T | M | T | P | ST | M | ST | T | P |

Where: M: 400 mg moxifloxacin; P: Placebo for relacorilant; T: Therapeutic dose (400 mg) of relacorilant; ST: Supra-Therapeutic dose (800 mg) of relacorilant.

In each period, subjects were admitted to the clinical site in the morning of Day-1 and stayed in the site until the morning of Day 6. In the study periods when subjects were randomized to Treatment T, ST, or P, the applicable study product (400 mg or 800 mg relacorilant or placebo for relacorilant) were taken once daily in the morning for 5 consecutive days. During the dosing period of positive control (Treatment M), placebo for relacorilant were administered on Days 1 to 4 to align with the dosing schedule for the other three treatments and moxifloxacin were administered in an open-labeled manner as a single dose in the morning of Day 5. Therefore, the treatment on Days 1 to 4 were double-blinded; it was not known before the morning on Day 5 whether or not a subject was allocated to receive moxifloxacin. Each dosing period (from Periods 2 to 4) was separated from the previous period by a washout period of at least 10 days from Day 6 of the previous period to Day 1 (first dose) of the subsequent period to prevent a carryover effect. The final visit was on Day 6 of Period 4. A safety phone follow-up was scheduled at 7 days (±2 days) post the final visit/early termination (ET) visit.

During each dosing period, 12-lead ECGs were performed and the data were extracted from a continuous recording (Holter) at scheduled time points for the measurement of heart rate and QTcF (corrected QT interval using Fridericia's formula) and other ECG intervals (PR and QRS intervals), and assessment of T-wave morphologies. The plasma concentrations of relacorilant, the metabolites of relacorilant, and moxifloxacin were analyzed using blood samples collected at scheduled time points that are time-matched to ECGs to evaluate the potential cardiodynamic effect of relacorilant.

Cardiodynamic ECG Assessment

In this study, 12-lead Holter equipment was used to obtain cardiodynamic ECG data, which was assessed by a blinded central ECG laboratory and safety ECGs were evaluated by the blinded investigator. All Holter ECG data was collected using a Global Instrumentation (Manlius, NY, USA) M12R ECG continuous 12 lead digital recorder. The continuous 12-lead Holter digital ECG data was stored onto secure digital memory cards. Extracted Holter ECGs were selected for use in the analyses at predetermined time points and were read centrally by a blinded central laboratory (ERT).

The ECG blinded central laboratory ("ERT") used the following principles for the analysis: ECG readers were blinded to the subject, visit and treatment allocation; a limited number of readers were employed for the study; baseline and on-treatment ECGs for a particular subject were over-read on the same lead and were analyzed by the same reader. The primary analysis lead was lead II. If lead II was not analyzable, then the primary lead of analysis was changed to another lead for the entire subject data set.

The following is a brief description of ECG analysis methods utilized by ERT.

TQT Plus ECG Extraction Technique

Ten 14-second digital 12-lead ECG tracings were extracted from the continuous Holter recordings using the 'TQT Plus method', a computer-assisted and statistical process utilized by ERT. The method enables extraction of ECGs with the lowest HR variability and noise within the protocol-specified extraction time window (e.g., the HR and QT changes from beat-to-beat in the range of <10%). At each protocol-specified time point, 10 ECG replicates were extracted from a 5-minute "ECG window" (typically, the last 5 minutes of the 15-minute period when the subject was maintained in a supine or semi-recumbent quiet position).

Expert-Precision QT Analysis

Expert-precision QT analysis were performed on all analyzable (non-artifact) beats in the 10 ECG replicates. Statistical quality control procedures are used to review and assess all beats and identify "high" and "low" confidence beats using several criteria, including: QT or QTc values exceeding or below certain thresholds (biologically unlikely); RR values exceeding or below certain thresholds (biologically unlikely); rapid changes in QT, QTc or RR from beat to beat.

Measurements of all primary ECG parameters (QT, QTc, RR) in all recorded beats of all replicates that are deemed "high confidence" were performed using iCOMPAS software (eResearch Technology, Inc., Philadelphia, PA, USA). All low confidence beats were reviewed manually and adjudicated using pass-fail criteria. The final QC assessment was performed by a cardiologist. The beats found acceptable by manual review were included in the analysis. The median QT, QTc, and RR value from each extracted replicate was calculated, and then the mean of all available medians from a nominal time point was used as the subject's reportable value at that time point.

Categorical T-wave morphology analysis and the measurement of PR and QRS intervals was performed manually in 3 of the 10 ECG replicates at each time point. Each fiducial point (onset of P-wave, onset of Q-wave, offset of S-wave, and offset of T-wave) was electronically marked. For T-wave morphology and U-wave presence, treatment-emergent changes were assessed, i.e., changes not present at baseline. For each category of T-wave morphology and of U-waves, the category was deemed as present if observed in any replicate at the time point. For baseline, the category was deemed as present if observed in any replicate from all time points that constitute baseline. The T-wave morphology categories are described as follows.

TABLE

T-wave Morphology and U-wave Presence Categories (Assessed Manually) Category Description

| | |
|---|---|
| Normal T-wave | Any positive T-wave not meeting any criterion below |
| Flat T-wave | T amplitude < 1 mm (either positive or negative) including flat isoelectric line |
| Notched T-wave (+) | Presence of notch(es) of at least 0.05 mV amplitude on ascending or descending arm of the positive T-wave |
| Biphasic | T-wave that contains a second component with an opposite phase that is at least 0.1 mV deep (both positive/negative and negative/positive and polyphasic T-waves included) |

TABLE-continued

| T-wave Morphology and U-wave Presence Categories (Assessed Manually) Category Description | |
|---|---|
| Normal T-wave (−) | T amplitude that is negative, without biphasic T-wave or notches |
| Notched T-wave (−) | Presence of notch(es) of at least 0.05 mV amplitude on descending or ascending arm of the negative T-wave |
| U-waves | Presence of abnormal U-waves |

Cardiodynamic ECG statistical analysis: ECG readings were performed in a blinded manner. The primary analysis was based on concentration-QTc modeling of the relationship between plasma concentrations of relacorilant (and applicable metabolite[s]) and the change-from-baseline of QTcF (ΔQTcF) with the intent to exclude an adverse effect of placebo-corrected ΔQTcF (ΔΔQTcF)>10 ms at clinically relevant plasma levels. In addition, the effects of relacorilant on the placebo-corrected ΔQTcF, ΔHR, ΔPR, and ΔQRS (ΔΔQTcF, ΔΔHR, ΔΔPR, and ΔΔQRS) were evaluated at each post-dosing time point ('by time point' analysis). An analysis of categorical outliers was performed for changes in QTcF, HR, PR, QRS, T-wave morphology, and U-wave presence. Assay sensitivity was evaluated by concentration-QTc analysis of the effect on ΔΔQTcF of moxifloxacin using a similar model as for the primary analysis. Assay sensitivity was deemed to be met where the slope of the concentration-QTc relationship was statistically significant at 10% level of significance in a 2-sided test and the predicted QT effect (i.e. the lower bound of the 2-sided 90% confidence interval of ΔΔQTcF) was above 5 ms at the observed geometric mean $C_{max}$ of 400 mg moxifloxacin.

Safety ECGs

Safety ECG assessment were performed according to the site's standard practice. Subjects rested in a supine position for at least 15 minutes before each time point of ECG assessment. Safety ECG were performed and evaluated by the investigator at screening, on Day-1 of each dosing period, and during each dosing period (Days 1 to 5), at 2, 6, and 8 hours post-dosing on Day 1, and at 2 hours post-dosing on Days 2 to 5, and before discharge on Day 6. The allowed time window for post-dose time point was ±15 minutes. The investigator or a designee trained in ECG reading reviewed the results of 12-lead ECG including heart rate, PR interval, RR interval, QRS duration, QT and QTcF interval, and gave an overall interpretation of the safety ECG assessment (normal, abnormal with clinical significance, or abnormal without clinical significance) at each time point. All clinically significant abnormal changes were recorded as AEs. Any clinically significant abnormal changes from baseline were followed until the abnormality was resolved or was adequately explained.

Results in Healthy Volunteers

QT prolongation is a significant concern for patients with CS. Approx. 26% of men with CS present with QT prolongation, and the risk of cardiac arrhythmic events correlates with the extent of QT prolongation. All currently approved medical treatments are associated with QT prolongation, posing a significant challenge for the management of CS. The results presented herein demonstrate the absence of QT prolongation with relacorilant, an investigational selective glucocorticoid receptor modulator, in healthy volunteers and patients with CS.

In a 3-part, single-center, First-in-Human study (NCT03508635, "phase 1 study"), 103 healthy volunteers received single or multiple ascending doses of relacorilant (up to 500 mg QD) for up to 14 days; 24 received placebo. In a randomized, partial double-blind, crossover Thorough QT study (NCT04795479, "TQT study"), the effect of multiple therapeutic (400 mg QD, n=25) and supra-therapeutic (800 mg QD, n=28) doses of relacorilant on cardiac repolarization was studied in healthy volunteers. A single dose of moxifloxacin (400 mg, n=28) was used as a positive control; 29 participants received placebo. In a single-arm, open-label phase 2 study (NCT02804750, "CS study"), 17 patients with CS received low-dose relacorilant (100-200 mg QD) for 12 weeks and 18 patients received high-dose relacorilant (250-400 mg QD) for 16 weeks. In all studies, ECG data were collected, and the heart rate-corrected QT interval using Fridericia's formula (QTcF) was assessed.

Baseline ECG parameters were within expectations for a healthy population across treatments with mean heart rate (HR) ranging from 58.7 to 60.7 beats per minute (bpm), mean QTcF from 405.6 to 407.2 msec, mean PR from 132.6 to 137.9 msec, and mean QRS ranging from 104.4 to 105.0 msec.

Relacorilant at the studied doses of 400 mg and 800 mg QD did not have a clinically relevant effect on HR. Least squares (LS) mean change-from-baseline in HR (ΔHR) on relacorilant followed the pattern observed on placebo. LS mean placebo-corrected ΔHR (ΔHR) across post-dose time points ranged from −3.2 bpm (at 12 hours post-dose on Day 1 in the 800 mg treatment) to 2.4 bpm (at 2 hours post-dose on Day 5 in the 800 mg treatment)

First-in-Human Study of Relacorilant

ECG data were available from 42 and 12 participants randomized to relacorilant or placebo, respectively, during the single ascending dose (SAD) phase, and from 34 and 12 participants randomized to relacorilant or placebo, respectively, during the multiple ascending dose (MAD) phase. Baseline mean (SD) QTcF values were within expectations for a healthy population (range 378.9.1 (11.7) msec to 403.5 (9.4) msec) and were similar in the respective relacorilant and placebo cohorts during the SAD and MAD study phases (see Table 1) (where the value in parentheses indicates standard deviation).

TABLE 1

ECG parameters of healthy volunteers randomized to relacorilant or placebo during the SAD and MAD phases in the phase 1 First-in-Human study.

| ECG parameter, msec | SAD Relacorilant[a] (n = 42) | SAD Placebo (n = 12) | MAD Relacorilant[b] (n = 34) | MAD Placebo (n = 12) |
|---|---|---|---|---|
| Baseline QTcF, mean (SD) | 378.9 (11.7) to 403.5 (9.4) | 399.0 (14.2) | 385.1 (14.1) to 401.8 (15.3) | 391.1 (12.1) |
| ΔQTcF, LS mean (90% CI) | −5.4 (−10.0, −0.0.8) to 1.1 (−1.6, 3.9) | −2.7, (−6.4, 1.1) to −1.7 (−4.0, 0.6) | −16.9 (−22.6, −11.2) to 1.7 (−2.7, 6.2) | −9.0 (−12.1, −5.9) to 3.5 (−0.2, 7.2)[c] |

TABLE 1-continued

ECG parameters of healthy volunteers randomized to relacorilant or placebo during the SAD and MAD phases in the phase 1 First-in-Human study.

| | SAD | | MAD | |
|---|---|---|---|---|
| ECG parameter, msec | Relacorilant[a] (n = 42) | Placebo (n = 12) | Relacorilant[b] (n = 34) | Placebo (n = 12) |
| ΔΔQTcF, LS mean (90% CI) | −3.5 (−7.2, 0.2) to 2.8 (−0.8, 6.4) | — | −12.3 (−20.2, −4.5) to 1.4 (−5.0, 7.9) | — |

Abbreviations: ΔQTcF = change from baseline QTcF; ΔΔQTcF = placebo-corrected change from baseline QTcF; CI = confidence interval; ECG = electrocardiogram; LS = least squares; MAD = multiple ascending dose; QTcF = QT interval corrected for heart rate using Fridericia's formula; SAD = single ascending dose.
[a]Data represent the range of mean (SD) QTcF or LS mean (90% CI) values for healthy volunteers who received a single dose of 5 mg, 15 mg, 50 mg, 150 mg, 300 mg, or 500 mg relacorilant during the SAD phase.
[b]Data represent the range of mean (SD) QTcF baseline or LS mean (90% CI) values for healthy volunteers who received 50 mg/day, 150 mg/day, 250 mg/day, or 500 mg/day relacorilant for 14 days during the MAD phase.
[c]Data represent the range of LS mean (90% CI) ΔQTcF values for healthy volunteers who received placebo for 14 days during the MAD phase.

Relacorilant did not have a clinically relevant adverse effect on QTcF during the SAD or MAD study phases. At all SAD and MAD post-dose time points and for all doses of relacorilant, LS mean ΔQTcF for relacorilant was similar to that for placebo. In both groups, post-dose LS mean placebo-corrected ΔQTcF (ΔΔQTcF) for relacorilant was small and mostly negative (Table 1). No obvious differences in ΔΔQTcF were observed for different relacorilant doses in SAD and MAD study phases, and mean ΔΔQTcF did not exceed 5 msec at any time point (FIGS. 3A-3E).

Figure 2A:
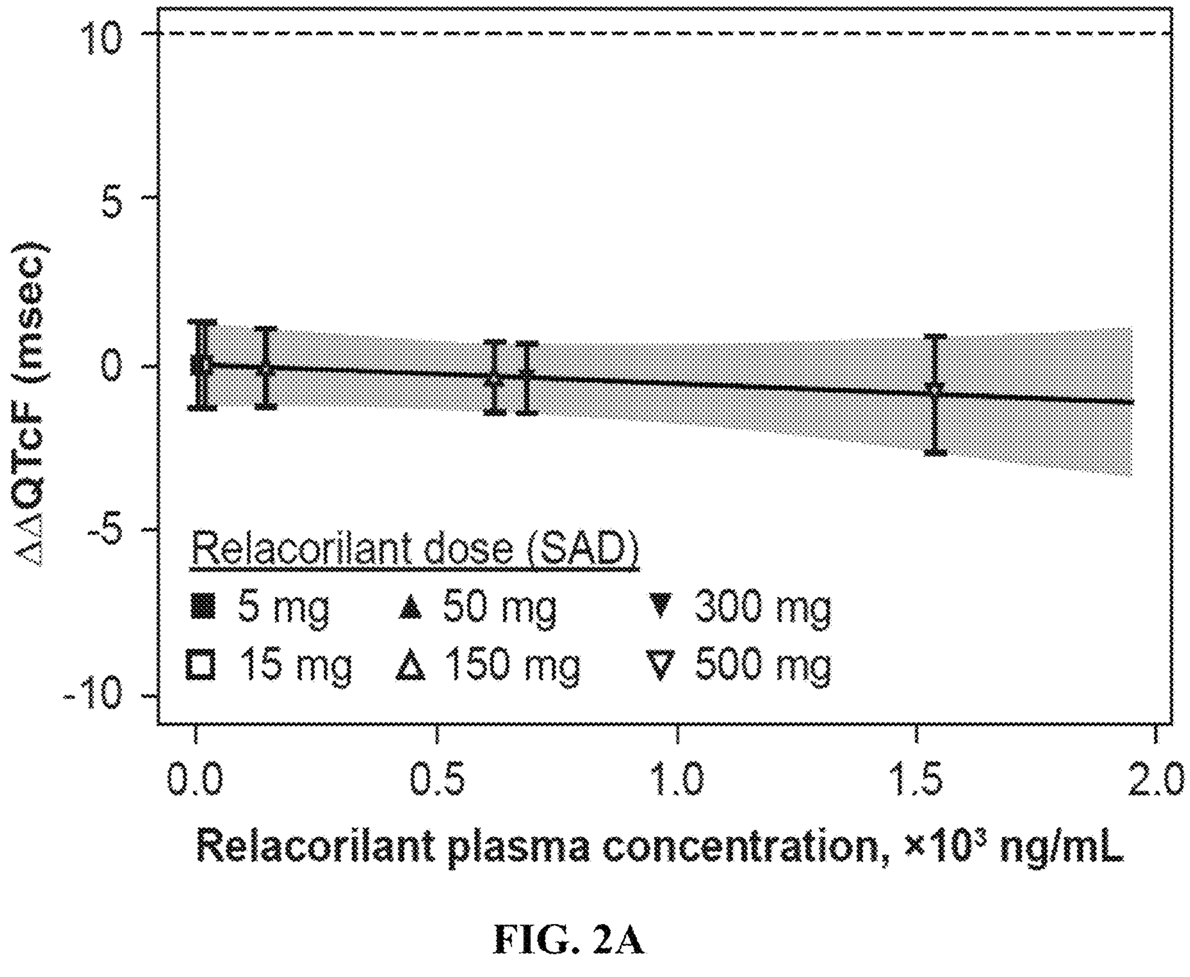
FIG. 2A shows the predicted change in geometric mean QTc for relacorilant doses of 50 milligrams (mg), 150 mg, 250 mg, and 500 mg for subjects in the Single Ascending Dose (SAD) study. The points with bars show the mean QTc values at $C_{max}$ (the time of highest relacorilant plasma concentration) for each dose ±90% confidence interval (CI) for those points; the line that links these geometric means shows the predicted mean ΔΔQTcF, and band around the line represents the 90% CI for that prediction. The placebo-corrected predicted change in QTc is less than 5 milliseconds (ms) for doses of 50, 150, 250, and 500 mg. Colored markers and error bars: Predicted mean (90% CI) ΔΔQTcF at the observed geometric mean relacorilant maximum concentration (Cmax). Dashed lines: 10-ms ΔΔQTcF effect threshold. Solid lines and gray shaded areas: Predicted mean ΔΔQTcF with 90% CI. CI, confidence interval. SAD equation: ΔΔQTcF=−0.005 (msec)−0.588 (msec/ng/ml)×relacorilant concentration (ng/ml). Abbreviations (throughout this application): ΔΔQTcF=placebo-corrected change in baseline QTcF; CI=confidence interval; $C_{max}$=maximum concentration; LS=least squares; MAD=multiple ascending dose; SAD=single ascending dose; QTcF=QT interval corrected for heart rate using Fridericia's formula.
Figure 2B:
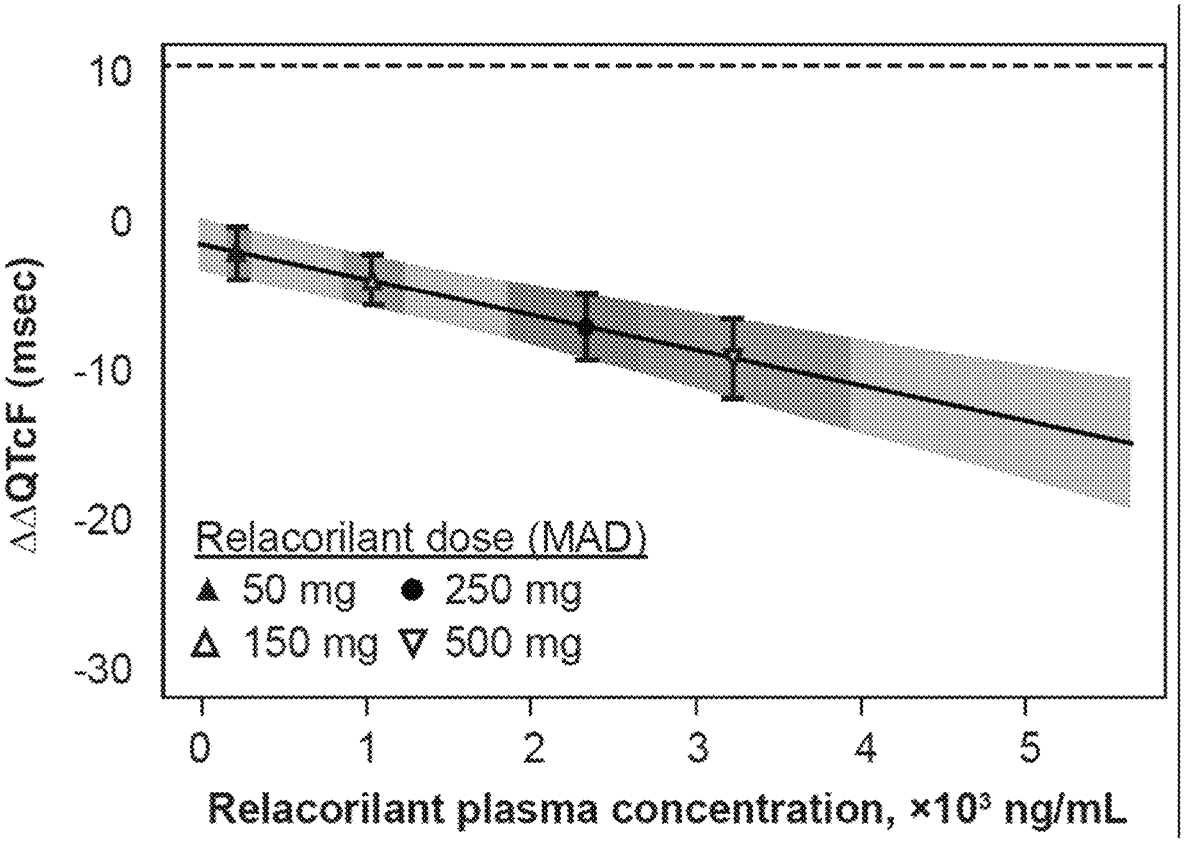
FIG. 2B shows the predicted change in geometric mean QTc for relacorilant doses of 50 milligrams (mg), 150 mg, 250 mg, and 500 mg for subjects in the Multiple Ascending Dose (MAD) study. The points with bars show the mean QTc values at $C_{max}$ (the time of highest relacorilant plasma concentration) for each dose ±90% confidence interval (CI) for those points; the line that links these geometric means shows the predicted mean ΔΔQTcF, and band around the line represents the 90% CI for that prediction. The placebo-corrected predicted change in QTc is less than 10 milliseconds (ms) for doses of 50, 150, 250, and 500 mg. Colored markers and error bars: Predicted mean (90% CI) ΔΔQTcF at the observed geometric mean relacorilant maximum concentration (Cmax). Dashed lines: 10-ms ΔΔQTcF effect threshold. Solid lines and gray shaded areas: Predicted mean ΔΔQTcF with 90% CI. CI, confidence interval. MAD equation: ΔΔQTcF=−1.804 (msec)−2.341 (msec/ng/mL)×relacorilant concentration (ng/ml).
Figure 3A:
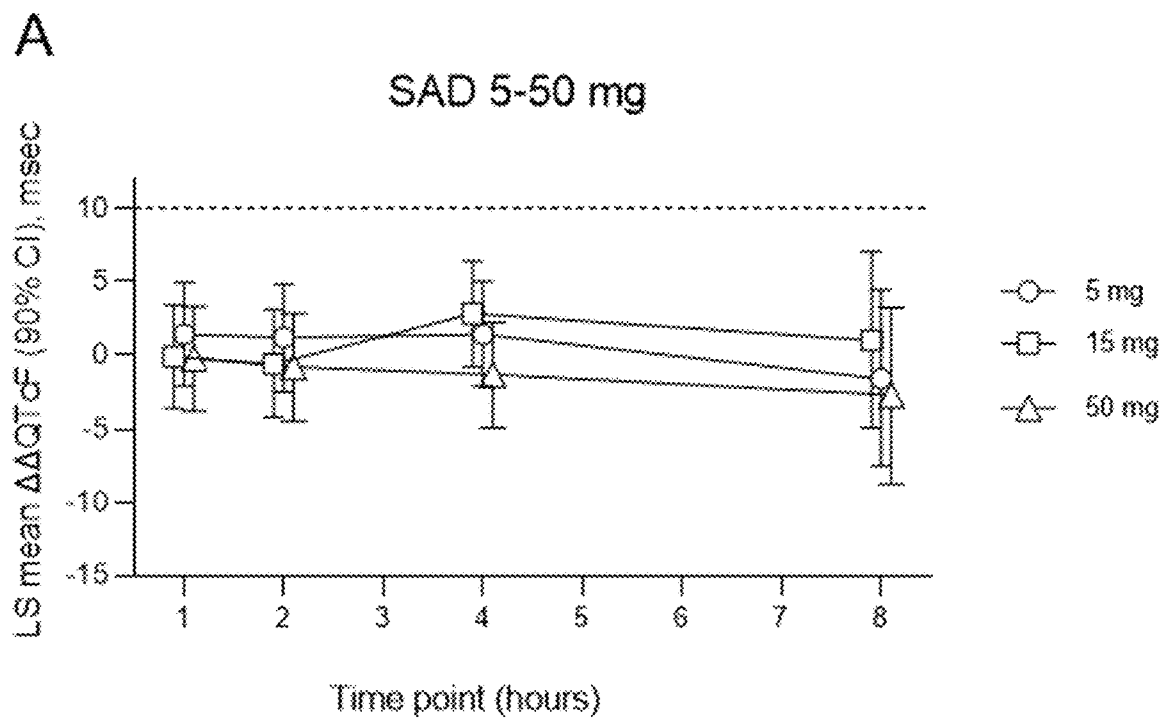
FIGS. 3A-3E show changes in QTc over a period of 8 hours after relacorilant administration. At 2 hours (the time of $C_{max}$), there was a slight decrease in QTc. Data were obtained from 103 healthy volunteers who received single or multiple ascending doses (SAD/MAD) of relacorilant (up to 500 mg QD) for up to 14 days; 24 healthy volunteers received placebo. Abbreviations: ΔΔQTcF=placebo-corrected change in baseline QTcF; CI=confidence interval; LS=least squares; MAD=multiple ascending dose; SAD=single ascending dose; QTcF=QT interval corrected for heart rate using Fridericia's formula.
Figure 3B:
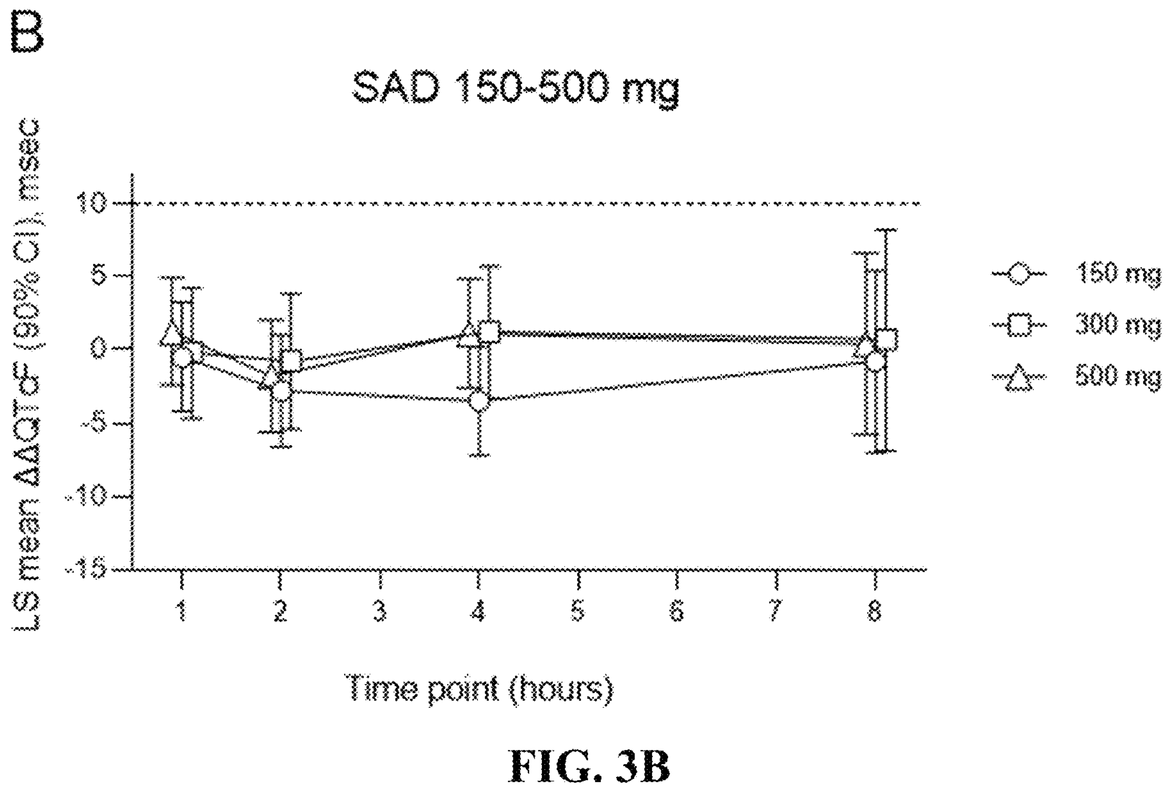
Figure 3C:
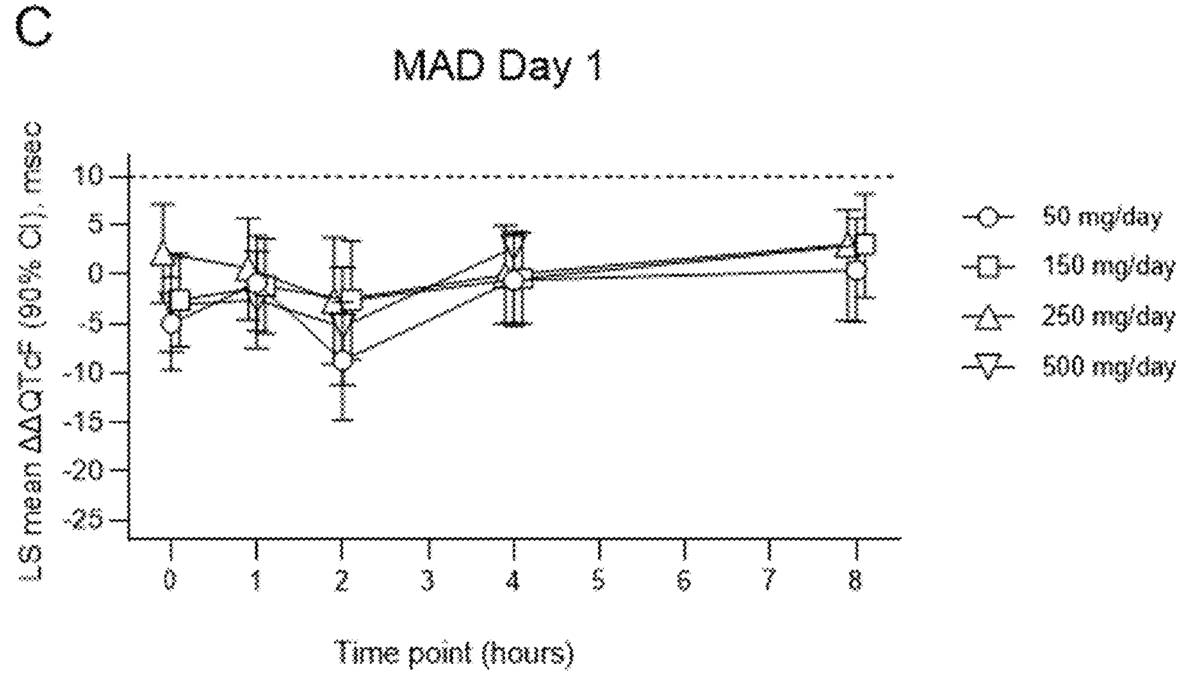
Figure 3D:
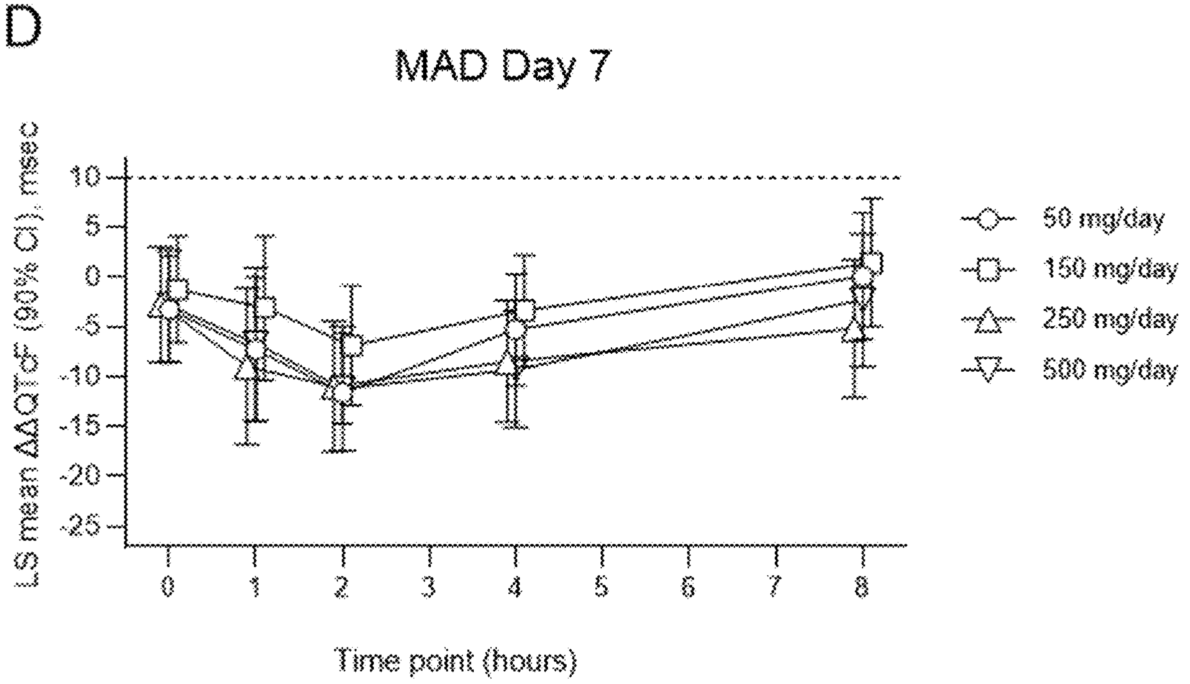
Figure 3E:
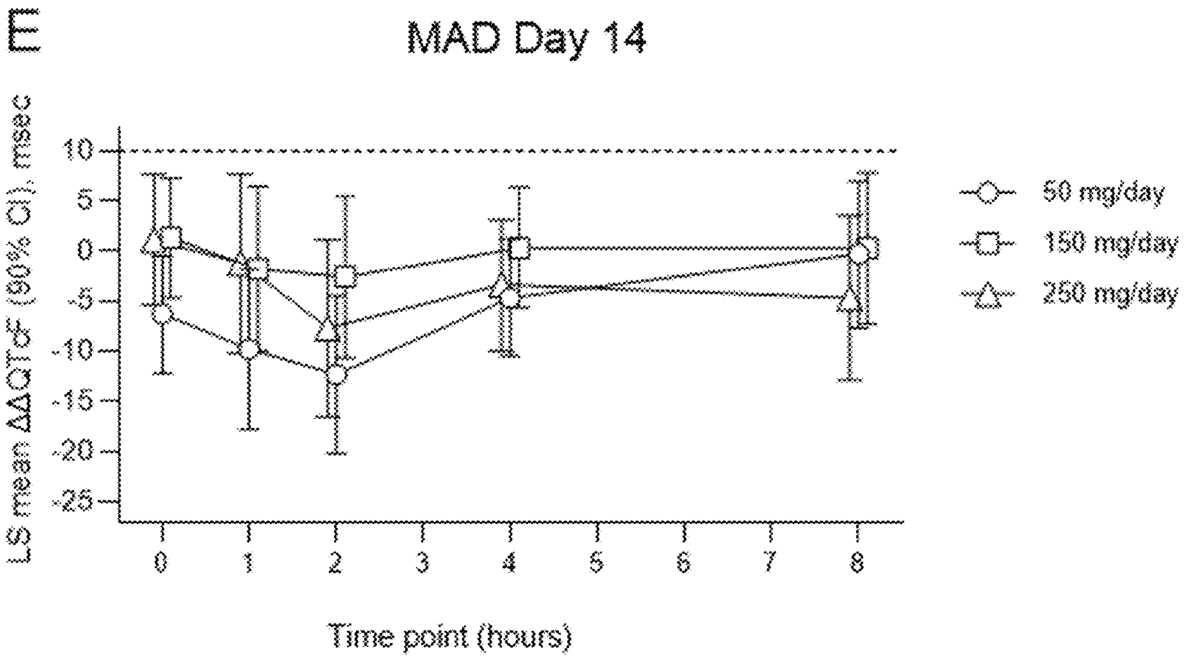

Relacorilant plasma concentration and QTcF data in the SAD and MAD phases were best fit with a linear model with treatment-specific intercepts. For both phases, the model-estimated slopes (90% CI) were slightly negative (SAD: $-0.59[-2.14, 0.97]\times10^{-3}$ msec/ng/ml; MAD: $-2.34[-3.16$ to $-1.52]\times10^{-3}$ msec/ng/ml). Therefore, a concentration-dependent effect of relacorilant on QTc prolongation was not identified. Exposure-response model-predicted results for mean ΔΔQTcF at peak plasma concentrations of relacorilant during the SAD and MAD phases also indicated that increasing doses of relacorilant were not associated with QT interval prolongation (FIGS. 2A and 2B). Based on the modeled SAD and MAD results, a prolonging effect of relacorilant on ΔΔQTcF exceeding the 10-msec threshold was excluded within the observed range of plasma concentrations up to approximately 4000 ng/ml (and no effect exceeding the 10-msec threshold were suggested by the data and modeling shown in FIGS. 2A and 5).

In the phase 1 study (First-in-Human study), relacorilant up to 500 mg daily did not have a clinically relevant adverse effect on ECG parameters. An adverse effect on placebo-corrected change from baseline QTcF (ΔΔQTcF) above 10 ms was excluded. In the TQT study, moxifloxacin control showed the expected QT prolongation, confirming assay sensitivity. Relacorilant had no clinically relevant effects on ECG parameters and showed effects similar to placebo. Based on concentration-QTc analysis, an adverse effect on ΔΔQTcF exceeding 10 ms was excluded within the full observed range of relacorilant plasma concentrations (a trend towards decreasing QT interval was noted at higher doses). The CS study confirmed that these favorable findings also apply to patients with CS: Throughout the CS study, no significant changes in median QTcF were observed in either dose group. In addition, no instances of hypokalemia were reported in the CS study. Based on the TQT study and supported by additional data in healthy volunteers and patients with CS, relacorilant did not show an association with QT prolongation.

Thus, no notable changes from baseline or between dose levels were observed in ECG parameters. Mean placebo-corrected ΔQTcF (ΔΔQTcF) did not exceed 3 ms at any time point in any of the dosing groups. A trend towards shorter QTc (towards reduced ΔΔQTcF) was observed at higher relacorilant concentrations (FIGS. 2A and 2B) At the time of the highest concentration (2 h), a reduction in ΔΔQTcF was observed (FIGS. 3A-3E). Based on exposure-response analysis, an adverse effect on placebo-corrected change from baseline QTcF greater than about 10 ms can be excluded (see FIGS. 2A and 2B).

Thorough QT/QTc Study ("TQT Study")

ECG data were available from 25 participants administered therapeutic (400 mg) relacorilant, 28 participants administered supra-therapeutic (800 mg) relacorilant, 29 participants who received placebo only, and 28 participants who received the moxifloxacin positive control. For all participants, mean (SD) QTcF values at baseline were within expectations for a healthy population (range 405.6 (15.33) msec to 407.2 (17.49) msec). On both days and for all post-dose time points with therapeutic and supra-therapeutic doses of relacorilant and with placebo, LS mean ΔQTcF was generally slightly negative (range −11.7 msec to 2.0 msec). In contrast, treatment with 400 mg moxifloxacin positive control on day 5 produced a rapid increase from LS mean (90% CI) pre-dose QTcF starting at 1 hour post-dose (5.7 (3.3, 8.2) msec) to a maximum observed value of 9.7 (7.2, 12.2) msec at 16 hours post-dose.

FIG. 4A shows the results of a TQT study on day 1 and day 5 of administration of relacorilant (400 mg (squares) or 800 mg (triangles) or of moxiflaxin (positive control; diamonds). Note that ΔΔQTcF appears to decline with time after relacorilant administration. These results exclude an adverse effect of relacorilant on ΔΔQTcF over 24 hours on day 1 or on day 5 of relacorilant administration. The dashed line shows the 10-msec ΔΔQTcF effect threshold.

FIG. 4B shows the results of a TQT study on day 5 of administration of relacorilant (400 mg (filled circles) or 800 mg (filled triangles) or of moxiflaxin (positive control; open circles). These results exclude an adverse effect of relacorilant on ΔΔQTcF over 24 hours after 5 days of relacorilant administration.

As shown in FIG. 4B, on day 5, LS mean (90% CI) ΔΔQTcF with both doses of relacorilant was negative at all post-dose time points, ranging from −8.0 (−11.5, −4.6) msec to −3.9 (−7.3, −0.5) msec. At all post-dose time points and with both doses of relacorilant, the upper bound of the 90% CI around the LS mean ΔΔQTcF was below the 10-msec ICH E14 threshold. On day 5, LS mean (90% CI) ΔΔQTcF for 400 mg moxifloxacin increased to a peak value of 10.7 (7.3, 14.1) msec at 1.5 hours post-dose. Consistent with regulatory expectations for a positive control, the lower bound of the 90% CI around the LS mean ΔΔQTcF for moxifloxacin exceeded 5 msec at 4 of the 12 post-dose time points.

As in the First-in-Human study, a linear model with a treatment effect-specific intercept provided the best fit to the relacorilant concentration and ΔΔQTcF data. The estimated slope (90% CI) of relacorilant plasma concentration in the concentration-QTc relationship was shallow and slightly negative (−0.97 (−1.68, −0.25)$\times10^{-3}$ msec/ng/ml) with a small treatment effect-specific intercept (90% CI) of −1.25 msec (−2.00, −0.51). At the geometric mean peak relacorilant concentration, the predicted effect on QTcF was −3.02 msec (90% CI: −4.16 to −1.88) and −3.87 msec (90% CI: −5.56 to −2.17) for the 400 mg dose ($C_{max}$ 1831.6 ng/ml) and 800 mg dose ($C_{max}$ 2705.5 ng/mL), respectively (FIG. 5).

TABLE 2

Predicted ΔΔQTcF Interval at Geometric Mean Peak Relacorilant and Moxifloxacin Concentration (PK/QTc Population)

| Treatment | n | Geometric Mean $C_{max}$ (ng/mL) | ΔΔQTcF Estimate (msec) (90% CI) |
|---|---|---|---|
| (T) Relacorilant 400 mg (Day 5) | 25 | 1831.6 | −3.02 (−4.16, −1.88)[1] |
| (ST) Relacorilant 800 mg (Day 5) | 27 | 2705.5 | −3.87 (−5.56, −2.17)[1] |
| (M) Moxifloxacin 400 mg single dose | 28 | 1869.4 | 8.90 (5.96, 11.85)[2] |

CI = Confidence Interval; msec = Millisecond; n = number of subjects used in calculations.
[1]Based on a linear mixed-effects model with ΔQTcF as the dependent variable, time-matched relacorilant plasma concentration as an explanatory variate, centered baseline QTcF as an additional covariate, treatment (relacorilant = 1 or placebo = 0) and time as fixed effects, and a random intercept and slope per subject.
[2]Based on a linear mixed-effects model with ΔQTcF as the dependent variable, time-matched moxifloxacin plasma concentration as an explanatory variate, centered baseline QTcF as an additional covariate, treatment (moxifloxacin = 1 or placebo = 0) and time as fixed effects, and a random intercept and slope per subject.

Based on the concentration-QTc modeling results, an effect on ΔΔQTcF exceeding the 10-msec threshold within the observed range of relacorilant plasma concentrations (up to ~4500 ng/mL with supra-therapeutic dosing) could be excluded.

FIG. 5 shows the shows the results (square and error bars (400 mg doses) and triangular and error bars (800 mg doses) and theoretical modeling (solid line and shaded area) of the TQT study, the results of which exclude an adverse effect (change greater than 10 msec) of relacorilant on ΔΔQTcF over the range of relacorilant concentrations up to about 4500 ng/mL. Markers and error bars: Estimated mean (90% CI) ΔΔQTcF at the observed geometric mean maximum relacorilant concentration with therapeutic (square) and supra-therapeutic (triangular) dosing. Dashed line: 10-ms ΔΔQTcF effect threshold. Solid line and shaded area: Predicted mean ΔΔQTcF with 90% CI, calculated from ΔΔQTcF=−1.2501 (msec)−0.97(x10-3 msec/ng/mL)×relacorilant concentration (ng/mL). This constitutes a negative TQT study, as described in the ICH E14 clinical guidance document (Guidance for Industry: E14 Clinical Evaluation of QT/QTc Interval Prolongation and Proarrhythmic Potential for Non-Antiarrhythmic Drugs, US Dept. HHS, 2005).

Phase 2 Study of Relacorilant in Patients with Cushing Syndrome ("CS Study")

The low- and high-dose relacorilant groups included 17 and 18 and patients, respectively. At baseline, mean (SD) QTcF ranged from 393.6 (16.5) msec to 394.2 (16.2) msec in the low-dose group and from 403.4 (36.3) msec to 409.9 (27.2) msec in the high-dose-group, confirming absence of QT prolongation at baseline. Throughout the study, median QTcF did not change appreciably in either group (FIGS. 6A and 6B). In both groups and for all doses of relacorilant, the mean (SD) ΔQTcF values were small and not statistically significant (range −2.2 (13.5) msec to 1.8 (24.4) msec; all P>0.3). In both groups, abnormal sinus tachycardia was the most common post-baseline ECG finding and was observed in 3 patients (17.6%) in the low-dose group and 2 patients (11.1%) in the high-dose group.

FIGS. 6A and 6B show the median QTcF values in CS patients receiving low doses of relacorilant (6A) and QTcF values in CS patients receiving high doses of relacorilant (6B). No significant changes in median QTcF were observed in either group.

Summary

In the First-in-Human study, relacorilant up to 500 mg QD showed no notable mean changes from baseline for any ECG parameters measured. No notable differences were observed between dose levels or relacorilant and placebo. No instances of post-dose QTcF interval>450 ms or a QTcF interval increase of >30 ms were reported. Change-from-baseline QTcF (ΔQTcF) was similarly small and mostly negative throughout the study and across dose groups; no dose-dependence was observed. An adverse effect of relacorilant on placebo-corrected ΔQTcF (ΔΔQTcF) above 10 ms was excluded for doses up to 400 mg/day. Exposure-response analysis showed a slightly negative relationship between relacorilant plasma levels and ΔΔQTcF, excluding a positive concentration dependent effect. Thus, relacorilant did not adversely affect ECG parameters in the First-in-Human Study.

In the TQT study, therapeutic and supra-therapeutic doses of relacorilant had no adverse effects on ECG parameters. Moxifloxacin positive control showed the expected rapid increase in QTc, confirming assay sensitivity. ΔQTcF values for therapeutic and supra-therapeutic relacorilant were generally similar to those for placebo. Based on concentration-QTc analysis, an adverse effect on ΔΔQTcF above 10 ms was excluded within the full observed range of relacorilant plasma concentrations (up to ~4500 ng/mL). Similar to the phase 1 study, the estimated slope of relacorilant concentration-QTc curve was shallow and negative, with a statistically significant treatment effect-specific intercept. relacorilant did not adversely affect ECG parameters in the TQT study; these results constitute a negative TQT study.

In the CS study, relacorilant had no adverse effects on ECG parameters. Throughout the study, no significant changes in median QTcF were observed in either dose group. Thus, the favorable QT findings of the studies in healthy volunteers were confirmed in patients with CS.

Across all 3 studies (First-in-Human, TQT, and CS studies), relacorilant was well tolerated. In the phase 1 study, Holter ECG data were collected in 44 study participants. Relacorilant up to 500 mg did not have an adverse effect on ECG parameters. An adverse effect on placebo-corrected change from baseline QTcF (ΔΔQTcF) above 10 ms was excluded. In the TQT study, the results of the moxifloxacin treatment confirmed assay sensitivity. Relacorilant had no adverse effects on ECG parameters and showed effects similar to placebo. Based on concentration-QTc analysis, an adverse effect on ΔΔQTcF exceeding 10 ms was excluded within the full observed range of relacorilant plasma concentrations. The CS study confirmed that these findings carry over to patients with CS. Throughout the study, no significant changes in median QTcF were observed in either group.

We have described here ECG results for relacorilant, an investigational drug for CS, from three studies: a First-in-Human study in healthy volunteers, a thorough QT/QTc study in healthy volunteers performed in accordance with regulatory guidance, and a phase 2 study over up to 16 weeks in patients with CS. All participants in the relacorilant studies had a normal QTc interval at screening and remained within the normal range while on-treatment. Overall, the results presented here demonstrate that relacorilant administration, including up to supra-therapeutic doses, has no effect on QTc interval prolongation in healthy volunteers or in patients with endogenous CS. In the First-in-Human study in heathy volunteers, there was no meaningful clinical effect of relacorilant on QTcF over the range of doses administered during the SAD and MAD phases. There was no discernable dose-dependency and LS mean ΔΔQTcF did not exceed 5 msec at any point during SAD and MAD study phases. The results of the concentration-QTc modeling further indicated that an effect on ΔΔQTcF exceeding 10 msec could be excluded for the range of observed plasma concentrations of relacorilant, up to approximately 4000 ng/mL. These results were confirmed in the dedicated placebo- and positive controlled thorough QT/QTc study of relacorilant at therapeutic and supra-therapeutic doses. As seen in the First-in-Human study, the effect of both therapeutic and supra-therapeutic relacorilant on ΔQTcF at all post-dose time points was similar to that of placebo. Also, for both doses, ΔΔQTcF was consistently small and generally slightly negative. Importantly, the upper bound of the two-sided 90% CI around the LS mean ΔΔQTcF for both doses of relacorilant was below 10 msec at all post-dose time points. In addition, results of concentration-QTc modeling excluded an effect on ΔΔQTcF exceeding 10 msec within the range of observed relacorilant plasma concentrations, up to approximately 4500 ng/mL seen with supra-therapeutic dosing. The ability of the thorough QT/QTc study to detect small increases in QTcF was confirmed by a lower bound>5 msec around the largest observed LS mean ΔΔQTcF for the moxifloxacin positive control. Taken together, these results constitute a negative QT/QTc study, as described by ICH E14 clinical regulatory guidance (U.S. Food and Drug Administration. E14 Clinical evaluation of QT/QTc interval prolongation and proarrhythmic potential for non-antiarrhythmic drugs—Questions and answers (R3). U.S. Department of Health and Human Services; 2017).

In both the First-in-Human and the Thorough QT/QTc studies, relacorilant administration was accompanied by slight downward trends in placebo-corrected ΔQTc. QTc intervals 390-450 msec in males and 390-460 msec in females have been suggested as the normal ranges, and it should be noted that all participants in the relacorilant studies had a normal QTc interval at screening and remained within the normal range while on-treatment.

The findings and conclusions of the 2 studies of relacorilant in healthy volunteers were additionally confirmed by the ECG results from the 16-week phase 2 study of relacorilant in patients with endogenous CS. At all time points and for all doses of relacorilant, mean ΔQTcF values for relacorilant were small and not statistically significant.

The absence of QTc prolongation with relacorilant presented here stands in contrast to most of the currently approved or widely prescribed therapies for CS (e.g., pasoreotide, levoketoconazole, and other drugs used to treat Cushing's syndrome).

In contrast to existing therapies for CS, relacorilant consistently demonstrated a lack of QTc prolongation in healthy volunteers and in patients with CS at all doses studied to-date, including supra-therapeutic doses. These results suggest that relacorilant should not present a risk of ventricular arrythmias and related sequalae, including sudden cardiac arrest. Thus, based on the data disclosed herein, relacorilant is not associated with QT prolongation and thus fulfills the previously unmet need for safe CS medications that do not cause QT prolongation and possibly fatal arrhythmias.

In addition to the patients discussed in this Example, no clinically significant QT prolongation was observed in a separate study in which at least 12 Cushing's syndrome patients received relacorilant while also receiving another drug, where that other drug was one known to cause QT prolongation (these drugs were fluoroquinoline, imidazole derivative, macrolide, or protease inhibitor drugs).

The present results show a trend toward reduced ΔΔQTcF at higher relacorilant concentrations, and, at the time of the highest concentration (2 h), a reduction in ΔΔQTcF was observed. These results indicate that relacorilant administration may be useful to reduce QT interval. These results thus indicate that relacorilant administration may be useful to treat patients, such as CS patients and others, suffering from QT interval prolongation.

All patents, patent publications, publications, and patent applications cited in this specification are hereby incorporated by reference herein in their entireties as if each individual publication or patent application were specifically and individually indicated to be incorporated by reference. In addition, although the foregoing invention has been described in some detail by way of illustration and example for purposes of clarity of understanding, it were readily apparent to those of ordinary skill in the art in light of the teachings of this invention that certain changes and modifications may be made thereto without departing from the spirit or scope of the appended claims.

The invention claimed is:

1. A method of treating a patient suffering from Cushing's syndrome or Cushing's Disease (collectively "CS") without significantly prolonging said patient's QT interval, where the QT interval is the duration of the time interval between the beginning of the QRS complex of the electrocardiogram (ECG) and the end of the T wave of the ECG, wherein a patient's QT interval is significantly prolonged if the QT interval is increased by more than 10 milliseconds (ms) from the patient's baseline QT interval, the method comprising:

Administering an effective amount of a heteroaryl ketone fused azadecalin compound, Wherein said treatment does not significantly prolong said patient's QT interval, Whereby the patient's CS is treated without significantly prolonging said patient's QT interval.

2. The method of claim 1, wherein said heteroaryl ketone fused azadecalin compound is relacorilant, which is (R)-(1-(4-fluorophenyl)-6-((1-methyl-1H-pyrazol-4-yl) sulfonyl)-4,4a,5,6,7,8-hexahydro-1H-pyrazolo[3,4-g]isoquinolin-4a-yl) (4-(trifluoromethyl)pyridine-2-yl) methanone, which has the structure:

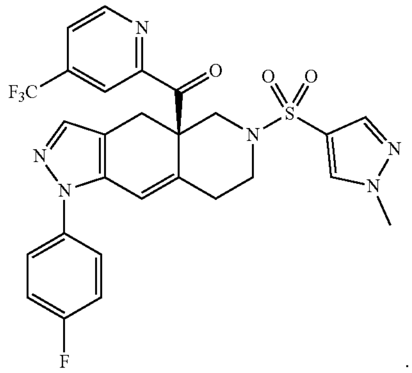 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

.

3. A method of reducing the effect on QT interval in a patient receiving a drug known to prolong the QT interval of the electrocardiogram (ECG) in some patients, where the QT interval is the duration of the time interval between the beginning of the QRS complex of the ECG and the end of the T wave of the ECG, and wherein a prolonged QT interval is a QT interval greater than about 450 ms in men or greater than about 460 ms in women, the method comprising:

Administering an effective amount of a heteroaryl ketone fused azadecalin compound to said patient receiving said drug known to prolong the QT interval of the electrocardiogram (ECG) in some patients, Whereby the effect of said drug on the QT interval of the patient is decreased.

4. The method of claim 3, wherein said heteroaryl ketone fused azadecalin compound is relacorilant, which is (R)-(1-(4-fluorophenyl)-6-((1-methyl-1H-pyrazol-4-yl) sulfonyl)-4,4a,5,6,7,8-hexahydro-1H-pyrazolo[3,4-g]isoquinolin-4a-yl) (4-(trifluoromethyl)pyridine-2-yl) methanone, which has the structure:

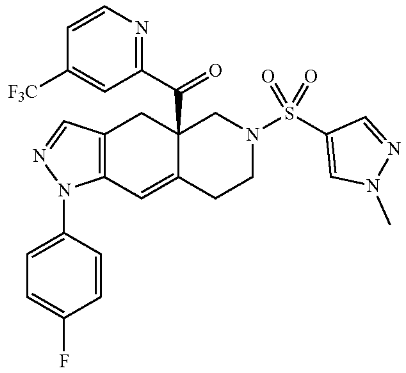

.

5. The method of claim 3, wherein said effective amount of a heteroaryl ketone fused azadecalin compound is between about 400 milligrams (mg) and about 800 mg of said heteroaryl ketone fused azadecalin compound.

6. The method of claim 3, wherein said effective amount of a heteroaryl ketone fused azadecalin compound is about 800 mg.

7. The method of claim 3, wherein the effective amount of the heteroaryl ketone fused azadecalin compound is an amount selected from the group consisting of between about 50 milligrams per day (mg/day) and about 800 mg/day, between about 50 mg/day and about 500 mg/day, and between about 400 mg/day and about 800 mg/day.

8. The method of claim 3, wherein said administration of an effective amount of said heteroaryl ketone fused azadecalin compound does not significantly increase the patient's risk of cardiac arrhythmia.

9. The method of claim 3, wherein said administration of an effective amount of said heteroaryl ketone fused azadecalin compound does not significantly increase the patient's risk of heart attack.

10. The method of claim 3, wherein said patient has been administered a medication that prolongs QT, and wherein said administration of an effective amount of said heteroaryl ketone fused azadecalin compound does not significantly increase the patient's risk of stroke.

11. The method of claim 3, wherein said administration of an effective amount of said heteroaryl ketone fused azadecalin compound does not significantly increase the patient's risk of sudden death.

12. The method of claim 3, wherein the heteroaryl ketone fused azadecalin compound is orally administered.

13. The method of claim 3, wherein said heteroaryl ketone fused azadecalin compound is administered to a fasted patient, where a fasted patient is one that has not eaten a meal for at least 4 hours prior to administration of the heteroaryl ketone fused azadecalin compound.

14. The method of claim 3, wherein between 50 mg/day and 400 mg/day of the heteroaryl ketone fused azadecalin compound is administered with food to a patient, or is administered to a fed patient, where a fed patient is one that has eaten a meal less than one hour prior to administration of the heteroaryl ketone fused azadecalin compound.

15. The method of claim 3, wherein said patient is male.

16. A method of treating a patient suffering from Cushing's syndrome or Cushing's Disease (collectively "CS") and suffering from prolonged QT interval, where the QT interval is the duration of the time interval between the beginning of the QRS complex of the electrocardiogram (ECG) and the end of the T wave of the ECG, and wherein a prolonged QT interval is a QT interval greater than about 450 ms in men or greater than about 460 ms in women, the method comprising:

Identifying the CS patient as suffering from prolonged QT interval,

Administering an effective amount of a heteroaryl ketone fused azadecalin compound, said effective amount being between about 400 milligrams (mg) and about 800 mg of said heteroaryl ketone fused azadecalin compound, Whereby the patient's CS and prolonged QT interval are treated.

17. The method of claim 16, wherein said heteroaryl ketone fused azadecalin compound is relacorilant, which is (R)-(1-(4-fluorophenyl)-6-((1-methyl-1H-pyrazol-4-yl) sulfonyl)-4,4a,5,6,7,8-hexahydro-1H-pyrazolo[3,4-g]isoquinolin-4a-yl) (4-(trifluoromethyl)pyridine-2-yl) methanone, which has the structure:

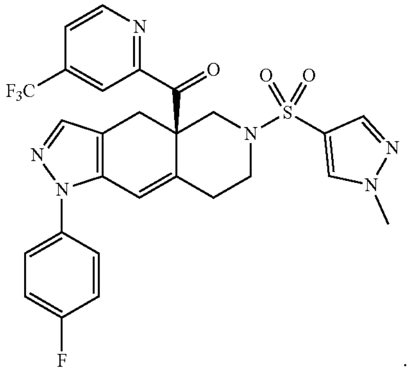 [SMILES: Cn1cc(S(=O)(=O)N2CCC3=Cc4c(cnn4-c4ccc(F)cc4)C[C@]3(C(=O)c3cc(C(F)(F)F)ccn3)C2)cn1]

.

18. The method of claim 16, wherein said effective amount of a heteroaryl ketone fused azadecalin compound is about 800 mg.

19. A method of decreasing the QT interval in a patient with a prolonged QT interval, where the QT interval is the duration of the time interval between the beginning of the QRS complex of the electrocardiogram (ECG) and the end of the T wave of the ECG, and wherein a prolonged QT interval is a QT interval greater than about 450 ms in men or greater than about 460 ms in women, the method comprising:

Administering an effective amount of a heteroaryl ketone fused azadecalin compound to said patient, Whereby the patient's QT interval is decreased.

20. The method of claim 19, wherein said heteroaryl ketone fused azadecalin compound is relacorilant, which is (R)-(1-(4-fluorophenyl)-6-((1-methyl-1H-pyrazol-4-yl) sulfonyl)-4,4a,5,6,7,8-hexahydro-1H-pyrazolo[3,4-g]isoquinolin-4a-yl) (4-(trifluoromethyl)pyridine-2-yl) methanone, which has the structure:

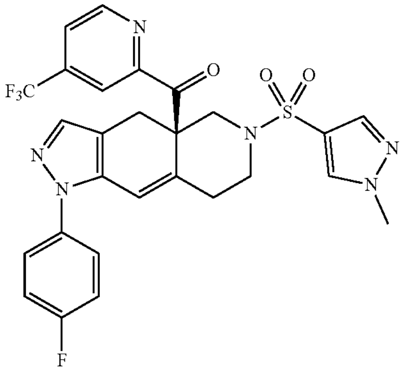

.

21. The method of claim 19, wherein said effective amount of a heteroaryl ketone fused azadecalin compound is between about 400 milligrams (mg) and about 800 mg of said heteroaryl ketone fused azadecalin compound.

22. The method of claim 19, wherein said effective amount of a heteroaryl ketone fused azadecalin compound is about 800 mg.

* * * * *